(12) United States Patent
Cary et al.

(10) Patent No.: US 7,910,309 B2
(45) Date of Patent: Mar. 22, 2011

(54) MULTIPLEXED LATERAL FLOW MICROARRAY ASSAY FOR DETECTION OF CITRUS PATHOGENS XYLELLA FASTIDIOSA AND XANTHOMONAS AXONOPODIS PV CITRI

(75) Inventors: R. Bruce Cary, Santa Fe, NM (US); Christopher J. Stubben, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 117 days.

(21) Appl. No.: 12/221,351

(22) Filed: Jul. 31, 2008

(65) Prior Publication Data

US 2010/0029496 A1 Feb. 4, 2010

(51) Int. Cl.
*C12Q 1/68* (2006.01)
(52) U.S. Cl. .......................................................... 435/6
(58) Field of Classification Search .................... None
See application file for complete search history.

(56) References Cited

U.S. PATENT DOCUMENTS 5,451,504 A 9/1995 Fitzpatrick et al.

OTHER PUBLICATIONS

U.S. Appl. No. 11/894,910, filed Aug. 27, 2007 in the name of Cary.
U.S. Appl. No. 61/126,640, filed May 5, 2008, in the name of Cary.
U.S. Appl. No. 61/126,645, filed May 5, 2008, in the name of Cary.
Andreotti, et al., "Immunoessay of infectious agents," Biotechniques Euro Edition, Oct. 2003, pp. 850-859, vol. 34, Issue 4.
Brlansky, et al., "Colonization of the Sharpshooter Vectors, *Oncometopia nigricans* and *Homalodisca coagulata* by Xylem-Limited Bacteria," The American Phytopathology Society, 1983, pp. 530-535, vol. 73, No. 4.
Brlansky, et al., "Transmission of the Citrus Variegated Chlorosis Bacterium *Xylella fastidiosa* with the Sharpshooter *Oncometopia nigricans*," Plant Disease, Nov. 2002, pp. 1237-1239, vol. 86, No. 11.
Carter, et al., "Lateral flow microarrays: a novel platform for rapid nucleic acid detection based on miniaturized lateral flow chromatography," Nucleic Acids Research, May 3, 3007, pp. 1-11, vol. 35, No. 10, Paper No. doi: 10.1093/nar/gkm2690.
Chang, et al., "Culture and Serological Detection of the Xylem-Limited Bacterium Causing Citrus Variegated Chlorosis and Its Identification as a Strain of *Xylella fastidiosa*,"Current Microbiology, 1993, pp. 137-142, vol. 27.
Ciapina, et al., "A nested-PCR assay for detection of *Xylella fastidiosa* in citrus pants and sharpshooter leafhoppers," Journal of Applied Microbiology, 2004, pp. 546-551, vol. 96, No. 3.
Cirino, et al, "Multiplex diagnostic platforms for detection of biothreat agents," Expert Rev. Mol. Diagn., 2004, pp. 841-857, vol. 4, No. 6.
Compton, J., "Nucleic acid sequence-based amplification," Nature, Mar. 7, 1991, pp. 91-92, vol. 350.
Cubero, et al., "Genetic Relationship among Worldwide Strains of *Xanthomonas* Causing Canker in Citrus Species and Design of New Primers for Their Indentification by PCR," Applied and Environmental Microbiology, Mar. 2002, pp. 1257-1264, vol. 68, Issue 3.
Cubero, et al., "Quantitative PCR Method for Diagnosis of Citrus Bacterial Canker," Applied and Environmental Microbiology, Jun. 2001, pp. 2849-2852, vol. 67, No. 6.
Davis, et al., "Pierce's Disease of Grapevines: Isolation of the Causal Bacterium," Science, Jan. 6, 1978, pp. 75-77, vol. 199.
Goheen, et al., "Association of a Rickettssialike Organism with Pierce's Disease of Grapevines and Alfalfa Dwarf and Heat Therapy of the Disease in Grapevines," Phytopathology, Mar. 1973, pp. 341-345, vol. 63.
Hartung, et al., "Detection of *Xanthomonas campestris* pv. Citri by the Polymerase Chain Reaction Method," Applied and Environmental Microbiology, Apr. 1993, pp. 1143-1148, vol. 59, No. 4.
Hartung, et al., Rapid and Sensitive Colorimetric Detection of *Xanthomonas axonopodis* pv. *Citri* by Immunocapture and a Nested-Polymerase Chain Reaction Assay, Phytopathology, 1996, pp. 95-101, vol. 86, No. 1.
Hendson, et al., "Genetic Diversity of Pierce's Disease Strains and Other Pathotypes of *Zylella fastidiosa*," Applied Environmental Microbiology, Feb. 2001, pp. 895-903, vol. 67, No. 2.
Hill, et al., "Acquisition and retention of *Xylella fastidiosa* by an Efficient Vector, *Graphocephala atropunctata*," Phytopathology, 1995, pp. 209-212, vol. 85, No. 2.
Hill, et al., "Populations of *Xylella fastidiosa* in Plants Required for Transmission by an Efficient Vector," Phytopathology, 1997, pp. 1197-1201, vol. 87, No. 12.
Hopkins, D.L., "*Xylella fastidiosa*: Xylem-Limited Bacterial Pathogen of Plants," Ann. Rev. Phytopathol., 1989, pp. 271-290, vol. 27.
Jacobi, et al., "Development of a multiplex immunocapture RT-PCR assay for detection and differentiation of tomato and tobacco mosaic tobamoviruses," Journal of Virological Methods, 1998, pp. 167-178, vol. 74, No. 2.
Kievits, et al., "NASBA™ isothermal enzymatic in vitro nucleic acid amplification optimized for the diagnosis of HIV-1 infection," Journal of Virological Methods, 1991, pp. 273-286, vol. 35.
Koch, Walter H., "Technology-Platforms for Pharmacogenomic Diagnostic Assays," Nature Reviews: Drug Discovery, Sep. 2004, pp. 749-762, vol. 3, No. 9.
Kohn, J., "An Immunochromatographic Technique," Immunology, 1968, pp. 863-865, vol. 15, No. 6.
Mackay, I.M., "Real-time PCR in the microbiology laboratory," Clinical Microbiology and Infection, Mar. 2004, pp. 190-212, vol. 10, No. 3.
Malek, et al., "Nucleic Acid Sequence-Based Amplification (NASBA™)," Methods in Molecular Biology, 1994, pp. 253-260, vol. 28.

(Continued)

*Primary Examiner* — Christopher M. Babic
(74) *Attorney, Agent, or Firm* — Kenneth K. Sharples

(57) ABSTRACT

The invention provides highly sensitive and specific assays for the major citrus pathogens *Xylella fastidiosa* and *Xanthomonas axonopodis*, including a field deployable multiplexed assay capable of rapidly assaying for both pathogens simultaneously. The assays are directed at particular gene targets derived from pathogenic strains that specifically cause the major citrus diseases of citrus variegated chlorosis (*Xylella fastidiosa* 9a5c) and citrus canker (*Xanthomonas axonopodis* pv citri). The citrus pathogen assays of the invention offer femtomole sensitivity, excellent linear dynamic range, and rapid and specific detection.

14 Claims, 9 Drawing Sheets

OTHER PUBLICATIONS

Pooler, et al., "Detection of *Xylella fastidiosa* in potential insect vectors by immunomagnetic separation and nested polymerase chain reaction," Letters in Applied Microbiology, 1997, pp. 123-126, vol. 25.

Pooler, et al., "Specific PCR Detection and Identification of *Xylella fastidiosa* Strains Causing Citrus Variegated Chlorosis," Current Microbiology, 1995, pp. 377-381, vol. 31, No. 6.

Purcell, et al., "Fastidious Xylem-Limited Bacterial Plant Pathogens," Annu. Rev. Phytopathol., 1996, pp. 131-151, vol. 34.

Purcell, et al., "Fate of Pierce's Disease Strains of *Xylella fastidiosa* in Common Riparian Plants in California," Plant Disease, 1999, pp. 825-830, vol. 83, No. 9.

Purcell, et al., "Pierce's Disease Bacterium: Mechanism of Transmission of Leafhopper Vectors," Science, Nov. 1979, pp. 839-841, vol. 206.

Rodrigues, et al., "Detection and Diversity Assessment of *Xylella fastidiosa* in Field-Collected Plant and Insect Samples by Using 16S rRNA and *gyrB* Sequences," Appl. Environ. Microbiol., 2003, pp. 4249-4255, vol. 69, No. 7.

Wells, et al., "Isolation, Culture, and Pathogenicity of the Bacteriumn Causing Phony Disease of Peach," Phytopathology, 1983, pp. 859-862, vol. 73, No. 6.

Yang, et al., "PCR-based diagnostics for infectious diseases: uses, limitations, and future applications in acute-care settings," The Lancet: Infectious Diseases, Jun. 2004, pp. 337-348, vol. 4, No. 6.

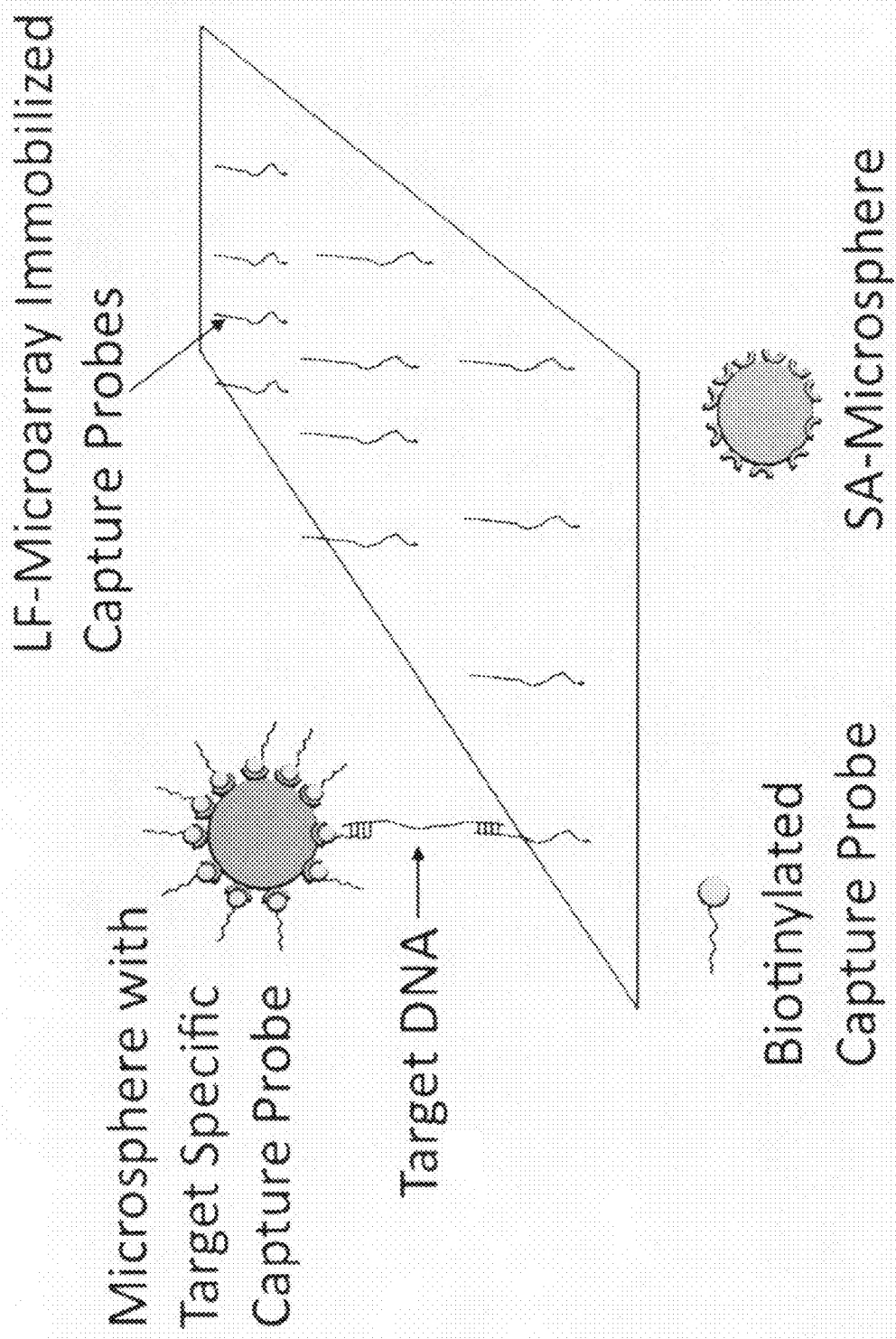

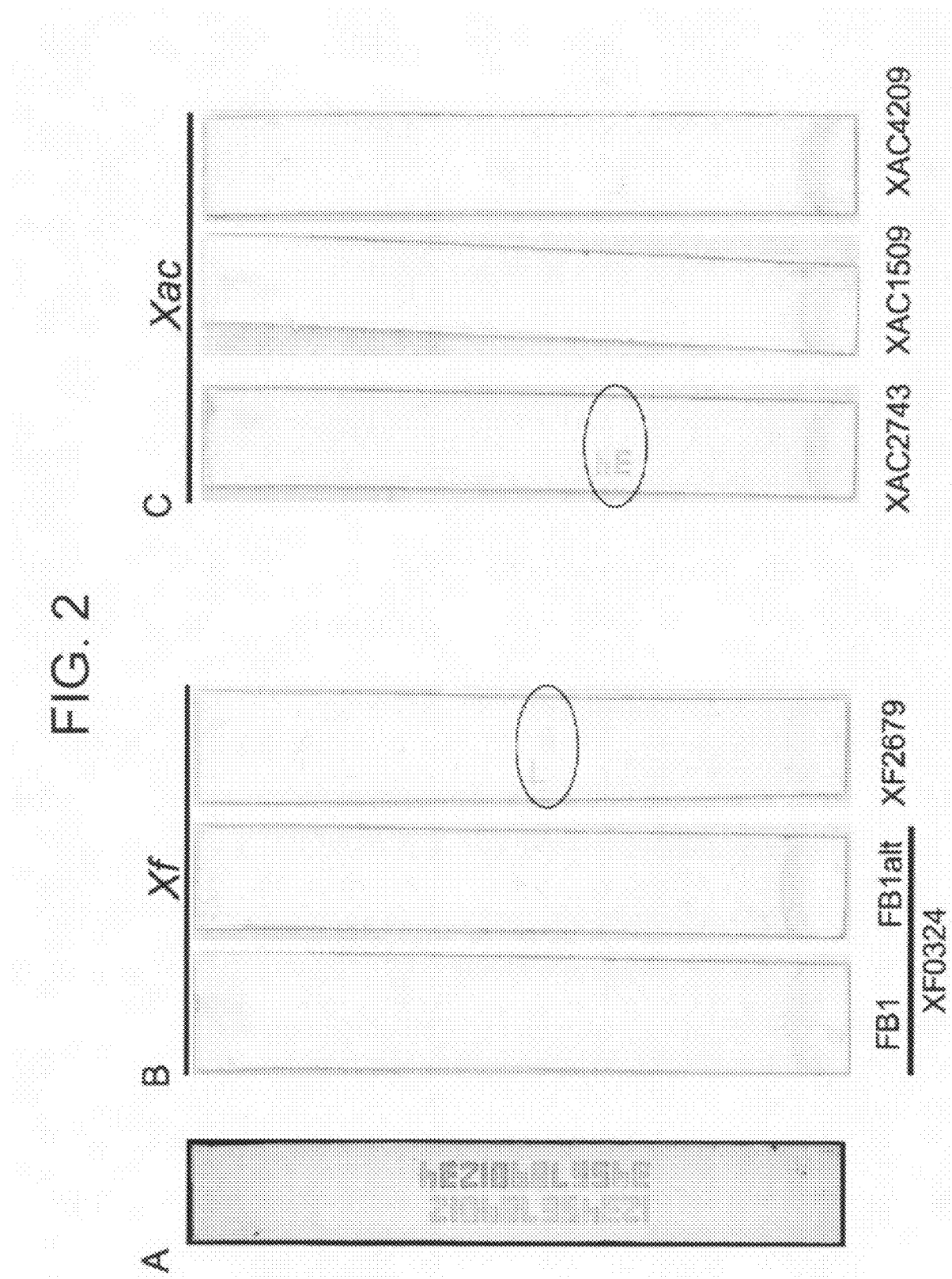

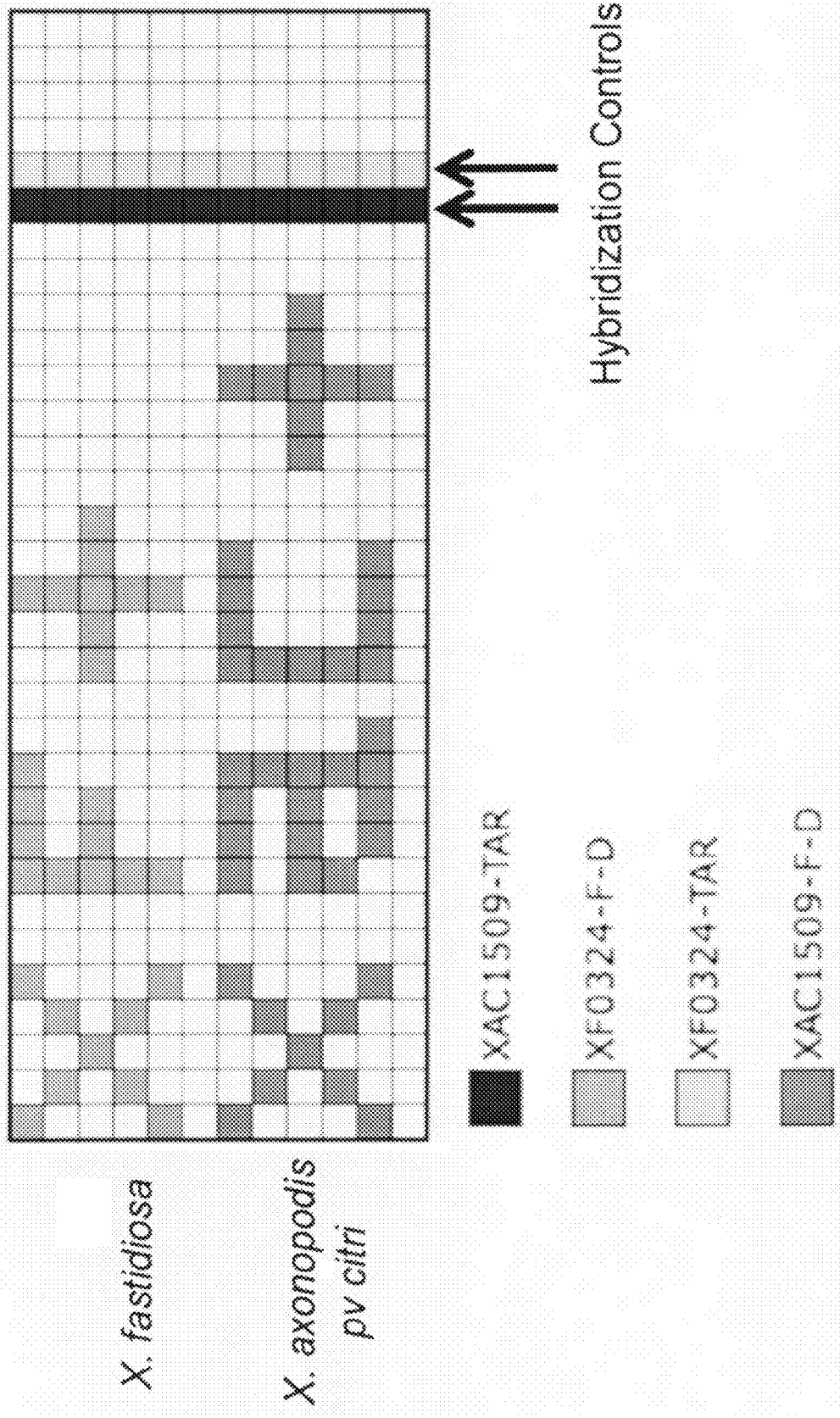

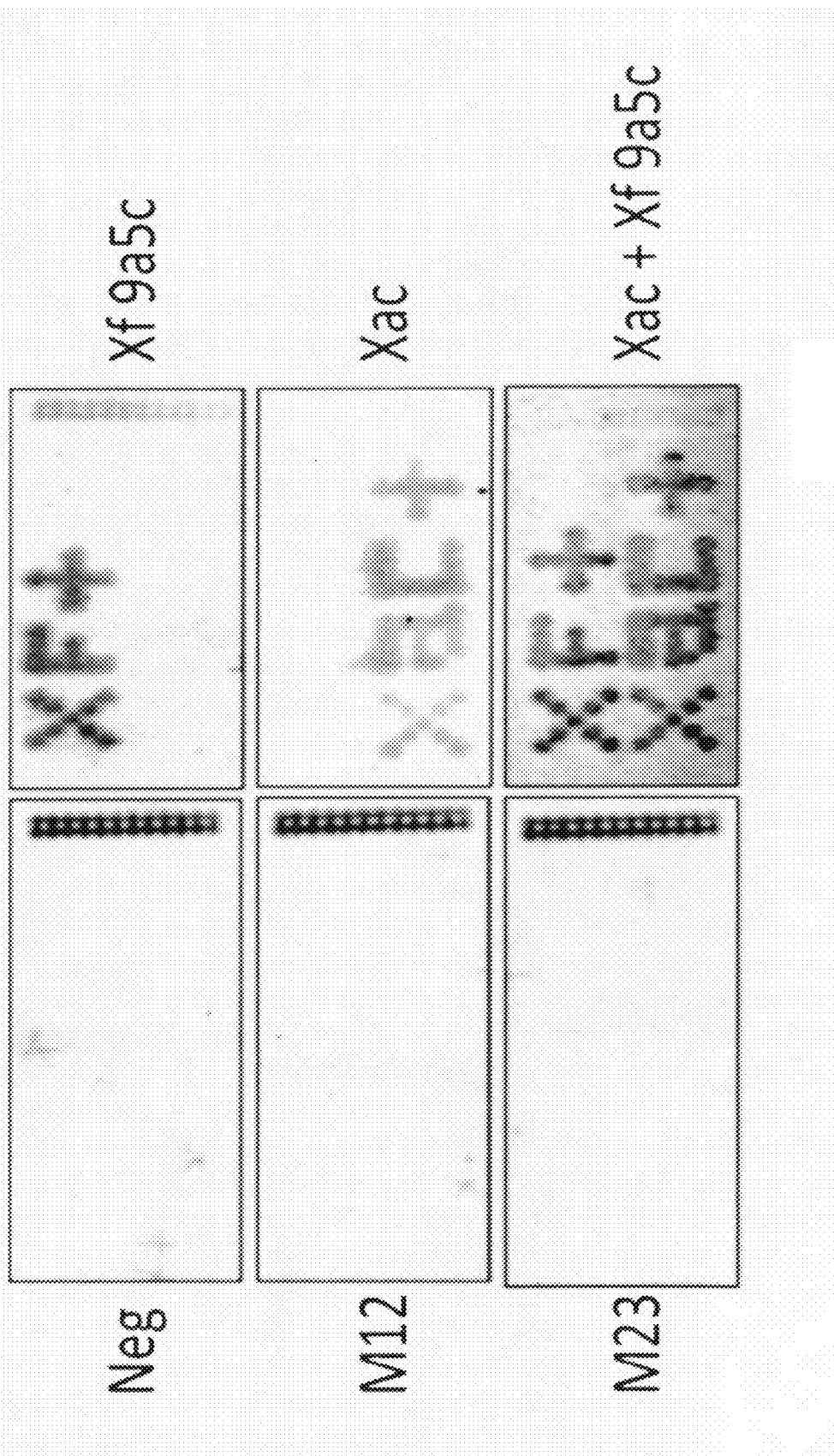

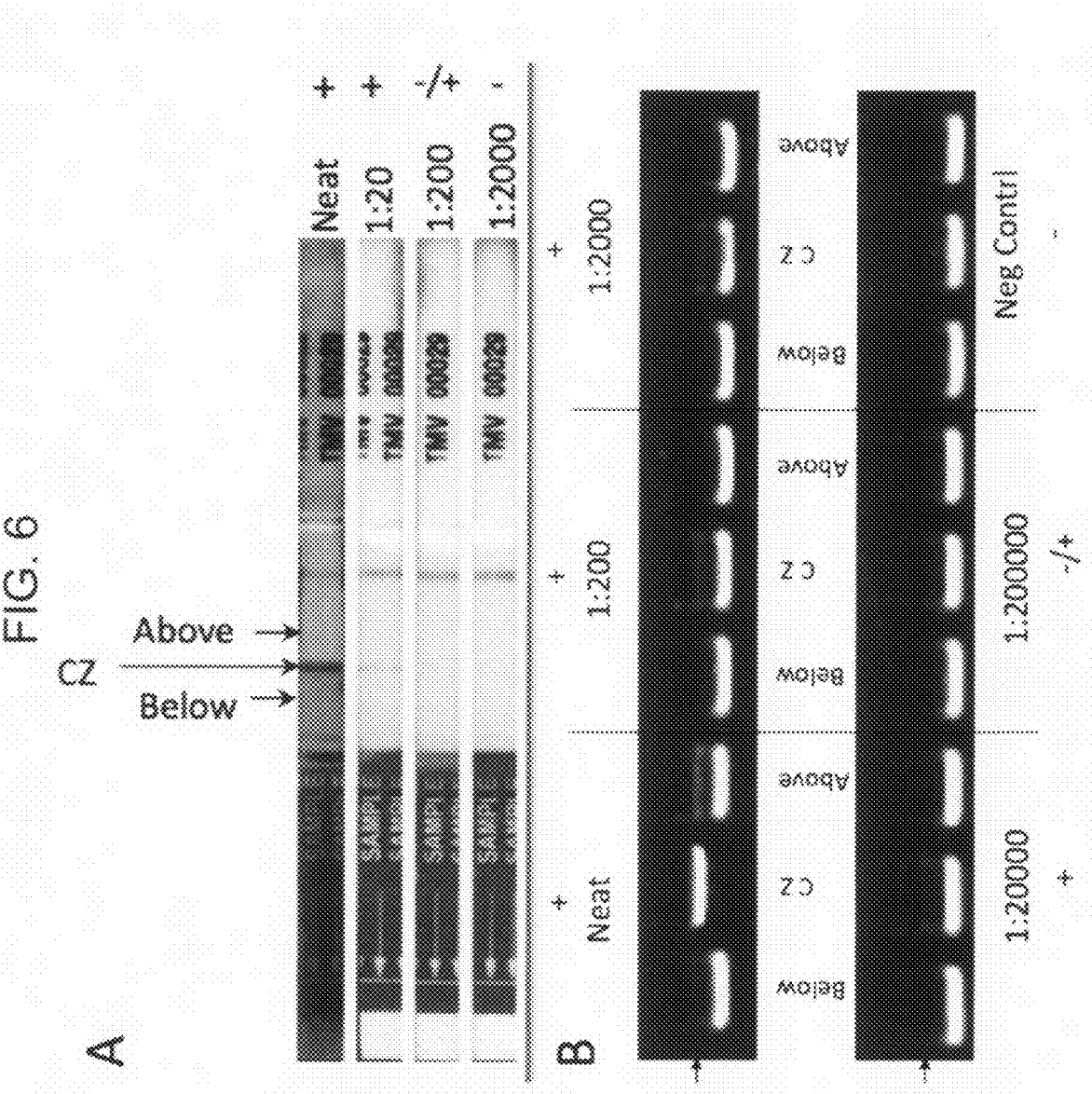

MULTIPLEXED LATERAL FLOW MICROARRAY ASSAY FOR DETECTION OF CITRUS PATHOGENS *XYLELLA FASTIDIOSA* AND *XANTHOMONAS AXONOPODIS PV CITRI*

STATEMENT AS TO RIGHTS TO INVENTIONS MADE UNDER FEDERALLY SPONSORED RESEARCH OR DEVELOPMENT

This invention was made with government support under Contract No. DE-AC52-06NA25396, awarded by the United States Department of Energy. The government has certain rights in this invention.

BACKGROUND OF THE INVENTION

The threat presented by plant and agricultural diseases of natural origin lend urgency to the development of rapid, field-deployable diagnostic tools capable of detailed genetic analyses. While immunoassays have long been available as rapid field-ready assays in the form of dipstick-like hand-held devices Kohn, J., 1968, *An immunochromatographic technique*. Immunology 15(6): 863-5), the sequence variation and exponential amplification accessible to nucleic acid-based methods are widely recognized as enabling a greater level of specificity and sensitivity than typically associated with immunoassay (Andreotti, et al., 2003, *Immunoassay of infectious agents*. Biotechniques. 35(4): 850-859).

Additionally, DNA or RNA-based diagnostics offer the potential for more detailed insights to the presence of antibiotic resistance elements, virulence genes and other high-resolution genetic information, including pre-symptomatic host biomarkers of infection, that may not be assayed immunologically. Unfortunately, technical hurdles associated with the field deployment of the requisite nucleic acid manipulations, including sample preparation, amplification and detection, have confounded migration of nucleic acid-based assays from the laboratory to the field (Yang and Rothman, 2004, *PCR-based diagnostics for infectious diseases: uses, limitations, and future applications in acute-care settings*. Lancet Infect Dis. 4(6): 337-48; Koch, W. H., 2004, *Technology platforms for pharmacogenomic diagnostic assays*. Nat Rev Drug Discov. 3(9): 749-761; Mackay, I. M., 2004, *Real-time PCR in the microbiology laboratory*. Clin Microbiol Infect. 10(3): 190-212; Cirino, et al., 2004, *Multiplex diagnostic platforms for detection of biothreat agents*. Expert Rev Mol Diagn. 4(6): p. 841-857).

Citrus is susceptible to a large number of diseases caused by plant pathogens. Economic losses due to plant diseases can be severe and are of particular concern in California and Florida, as well as in Brazil. In the state of Florida, citrus fruits, including oranges, grapefruit, tangelos, tangerines, limes, and other specialty fruits, are the state's largest agricultural commodity. Florida is the world's leading producing region for grapefruit and second only to Brazil in orange production. Florida produces over 80 percent of the United States' supply of citrus.

Citrus canker is a very serious disease affecting most commercial citrus varieties, and is caused by the bacterial pathogen *Xanthomonas axonopodis* pv. *citri* ("Xac"). The pathogen causes necrotic lesions on leaves, stems and fruit. Severe infections can cause defoliation, badly blemished fruit, premature fruit drop, twig dieback and general tree decline. Considerable regulatory effort is directed at preventing the spread of citrus canker because it is not present in all citrus-growing regions of the world where the climate is conducive to its development. Xac's presence, if detected, triggers immediate quarantines of areas with outbreaks, disrupting movement of fresh fruit. Eradication has typically involved burning uprooted trees.

There are several distinct types of citrus canker disease caused by various pathovars and variants of Xac. The Asiatic type of canker (Canker A), caused by a group of strains originally found in Asia, is by far the most widespread and severe form of the disease. This is the group of *X. axonopodis* pv. *citri* strains that causes the disease most referred to as Asiatic citrus canker. Minor genetic variation of citrus canker strains has been detected in the A strains in Florida and other citrus growing regions of the world, which may be exploited to identify their origin when introduced into new locations.

PCR-based methods for Xac detection have been described and are currently in use (Cubero, et al., 2001, Quantitative PCR method for diagnosis of citrus bacterial canker. Appl. Environ. Microbiol. 67:2849-2852; Hartung and Pruvost, 1993, Detection of *Xanthomonas campestris* pv. *citri* by the polymerase chain reaction. Appl. Environ. Microbiol. 59:1143-1148). The primers used for citrus canker diagnosis are based on the plasmid containing the pthA gene, the primary virulence element in all citrus canker strains (Hartung, et al., 1996, Phytopathology 86:95-101). Primers based on the pthA gene are available for detection of all canker strains in Florida and elsewhere (Cubero and Graham, 2002, Appl. Environ. Microbiol. 68:1257-1264). Unfortunately, these same primers generate a PCR product of the same size in Xanthomonads not currently thought to cause citrus canker, limiting their utility for real-world applications where contaminating microbial flora may generate a false positive using this assay (Cubero and Graham, 2002, Appl. Environ. Microbiol. 68:1257-1264). Additionally, the use of a plasmid derived sequences may be undesirable due to the increased potential for horizontal gene transfer.

Primers for the identification of Xac based upon the internally transcribed spacer between 16S and 23S rRNA genes have also been reported. Again, however, this set of primers generates an amplicon from *X. axonopodis* pv *citri* and not other Xanthomonads cultured from citrus tissue, but lacks specificity within the broader diversity found within *Xanthomonas* spp. resulting in false positive signals when challenged with some other Xanthomonads. These characteristics render such assays of utility only for the identification of Xac from among bacteria isolated and cultured from citrus tissue not for the detection and identification of bacteria on plant samples.

Additionally, all of the available assays rely on PCR technology and fluorescent detection of amplified nucleic acids, which requires the use of complex laboratory instrumentation and involve high per assay cost (Yang and Rothman, 2004, PCR-based diagnostics for infectious diseases: uses, limitations, and future applications in acute-care settings. *Lancet Infect Dis*. 4: 337-348: Koch, W. H., 2004, Technology platforms for pharmacogenomic diagnostic assays. *Nat Rev Drug Discov*. 3: 749-761; Mackay, I. M., 2004, Real-time PCR in the microbiology laboratory. *Clin Microbiol Infect*. 10: 190-212; Cirino, et al., 2004, Multiplex diagnostic platforms for detection of biothreat agents. *Expert Rev Mol Diagn*. 4: 841-857). Existing technologies, therefore, are not amenable to field deployment, which remains a significant unmet need.

Citrus variegated chlorosis (CVC) is another major disease affecting citrus in Brazil and Florida, as well as other citrus growing regions (Chang et al., 1993, Curr. Microbiol. 27: 137-142). In Brazil, it was estimated to have been present in over one-third of the 200 million citrus trees in the state of Sao Paulo in 2001 (Brlansky et al., 2002, Plant Disease 86(11): 1237-39). CVC causes severe leaf chlorosis between veins.

Infected citrus trees typically exhibit attenuated vigor and growth, and show abnormal flowering and fruit sets. Fruits in CVC-infected trees are often small, hard and of high acid content, thus rendering them unsuitable for markets or juice processing. As trees mature, the disease typically spreads from one limb to another, and eventually to the entire tree. Eradication measures are extreme, and include the removal of entire orchards upon a threshold level of infection (in Brazil, for example, that threshold is 30%).

CVC is caused by the bacterial pathogen *Xylella fastidiosa* (Xf), which also causes a number of other diseases in commercial crops, including Pierce's Disease in grapevines (Davis et al., 1978, Science 199: 75-77), alfalfa dwarf disease (Goheen et al., 1973, Phytopathology 63: 341-345), and leaf scorch disease or dwarf syndromes in numerous other agriculturally significant plants, including almonds, coffee, and peach (Hopkins, 1989, Annu. Rev. Phytopathol. 27: 271-290; Wells et al., 1983, Phytopathology 73: 859-862; De Lima, et al., 1996, Fitopatologia Brasileira 21(3)). Although many agriculturally important plants are susceptible to diseases caused by Xf, in the majority of plants Xf behaves as a harmless endophyte (Purcell and Saunders, 1999, Plant Dis. 83: 825-830). Strains of Xf are genetically diverse and pathogenically specialized (Hendson, et al., 2001, Appl. Environ. Microbiol 67: 895-903). For example, certain strains cause disease in specific plants, while not in others. Additionally, some strains will colonize a host plant without causing the disease that a different Xf strain causes in the same plant.

Xf is acquired and transmitted to plants by leafhoppers of the Cicadellidae family and spittlebugs of the Cercropidae family (Purcell and Hopkins, 1996, Annu. Rev. Phytopathol. 34: 131-151). Once acquired by these insect vectors, Xf colonies form a biofilm of poorly attached Xf cells inside the insect foregut (Briansky et al., 1983, Phytopathology 73: 530-535; Purcell et al., 1979, Science 206: 839-841). Thereafter, the insect vector remains a host for Xf propagation and a source of transmission to plants (Hill and Purcell, 1997, Phytopathology 87: 1197-1201). In susceptible plants, Xf multiplies and spreads from the inoculation site into the xylem network, where it forms colonies that eventually occlude xylem vessels, blocking water transport. Prior studies have suggested that the presence of as few as 100 Xf cells in an insect vector is sufficient to enable transmission of the agent to a susceptible plant (Hill and Purcell, 1995, Pytopathology 85: 209-212). The low titer of Xf that can confer infection presents a challenge for commonly deployed serological diagnostics, e.g. ELISA, which typically require titers in excess of 1000 cells/ml for reliable detection.

For the sensitivity required to detect Xf in both plant and insect vector tissues a molecular assay must be used. Available molecular assays for the detection of Xf rely upon PCR assay platforms, and are therefore limited in their utility and field-deployability (Rodrigues, et al., 2003, "Detection and diversity assessment of *Xylella fastidiosa* in field-collected plant and insect samples by using 16S rRNA and gyrB sequences." Appl Environ Microbiol 69(7): 4249-55; Ciapina, et al., 2004, "A nested-PCR assay for detection, of *Xylella fastidiosa* in citrus plants and sharpshooter leafhoppers." J Appl Microbiol 96(3): 546-51; Pooler, et al., 1997, "Detection of *Xylella fastidiosa* in potential insect vectors by immunomagnetic separation and nested polymerase chain reaction." Lett Appl Microbiol 25(2): 123-6; Pooler, M. R. and J. S. Hartung, 1995, "Specific PCR detection and identification of *Xylella fastidiosa* strains causing citrus variegated chlorosis." Curr Microbiol 31(6): 377-81). The development of a sensitive isothermal assay for Xf would increase the simplicity of Xf detection and provide a protocol easily adaptable to a field deployable detection system.

SUMMARY OF THE INVENTION

The invention provides highly sensitive and specific assays for the major citrus pathogens *Xylella fastidiosa* and *Xanthomonas axonopodis*, including a field deployable multiplexed assay capable of rapidly assaying for both pathogens simultaneously. The assays are directed at particular gene targets derived from pathogenic strains that specifically cause the major citrus diseases of citrus variegated chlorosis (*Xylella fastidiosa* 9a5c) and citrus canker (*Xanthomonas axonopodis* pv *citri*).

In preferred embodiments of the assays of the invention, the recently described lateral flow microarray assay platform "LFM" is employed, together with novel primers designed to amplify highly specific polynucleotide target sequences for each of these pathogens.

Accordingly, in one aspect, the invention provides an assay for detecting the presence of *Xylella fastidiosa* strain 9a5c in a citrus plant, an environmental sample or an insect, comprising (a) extracting or releasing nucleic acid from a sample of the citrus plant, environmental sample or insect; (b) amplifying a XF0324 gene target nucleic acid using nucleic acid sequence based amplification (NASBA) with the amplification primers of SEQ ID NOS: 1 and 2, to generate a solution containing amplified single-stranded RNA amplification product complementary to the target nucleic acid, if present in the nucleic acid from the sample; and, (c) detecting the presence of the RNA amplification product in a lateral flow chromatographic device which uses nucleic acid sandwich hybridization, wherein, (i) a detectably-labeled detection oligonucleotide which comprises a sequence complementary to a first sequence of the RNA amplification product, is used in combination with (ii) a capture oligonucleotide which is immobilized on a detection membrane in the lateral flow chromatographic device and which comprises a sequence complementary to a second sequence of the RNA amplification product. In a particular embodiment, the capture oligonucleotide comprises the sequence of SEQ ID NO: 3 or nucleotides 16-37 thereof. In another particular embodiment, the detection oligonucleotide comprises the sequence of SEQ ID NO: 4 or nucleotides 1-20 thereof. In yet another particular embodiment, the capture oligonucleotide comprises the sequence of SEQ ID NO: 3 or nucleotides 16-37 thereof, and the detection oligonucleotide comprises the sequence of SEQ ID NO: 4 or nucleotides 1-20 thereof. Further, methods of diagnosing citrus variegated chlorosis in a citrus plant are provided, comprising detecting *Xylella fastidiosa* strain 9a5c using the foregoing assays.

In another aspect, the invention provides an assay for detecting the presence of *Xanthomonas axonopodis* pv. *citri* in a citrus plant, an environmental sample or an insect, comprising (a) extracting or releasing nucleic acid from a sample of the citrus plant, environmental sample or insect; (b) amplifying a XAC1509 gene target nucleic acid using nucleic acid sequence based amplification (NASBA) with the amplification primers of SEQ ID NOS: 6 and 7, to generate a solution containing amplified single-stranded RNA amplification product complementary to the target nucleic acid, if present in the nucleic acid from the sample; and, (c) detecting the presence of the RNA amplification product in a lateral flow chromatographic device which uses nucleic acid sandwich hybridization, wherein, (i) a detectably-labeled detection oligonucleotide which comprises a sequence complementary to a first sequence of the RNA amplification product, is used in combination with (ii) a capture oligonucleotide which is immobilized on a detection membrane in the lateral flow chromatographic device and which comprises a sequence complementary to a second sequence of the RNA amplification product. In a particular embodiment, the capture oligonucleotide comprises the sequence of SEQ ID NO: 8 or nucleotides 16-35 thereof. In another particular embodiment, the detection oligonucleotide comprises the sequence of SEQ ID NO: 9 or nucleotides 1-21 thereof. In yet another particular embodiment, the capture oligonucleotide comprises the sequence of SEQ ID NO: 8 or nucleotides 16-35 thereof and the detection oligonucleotide comprises the sequence of SEQ ID NO: 9 or nucleotides 1-21 thereof. Further, methods of diagnosing citrus variegated chlorosis in a citrus plant are provided, comprising detecting *Xanthomonas axonopodis* pv. *citri* using the foregoing assays.

In yet another aspect, the invention provides a multiplex assay for detecting the presence of a Citrus Variegated Chlorosis-associated strain of *Xylella fastidiosa* and/or a Citrus Canker-associated strain of *Xanthomonas axonopodis* in a citrus plant, an environmental sample or an insect, comprising (a) extracting or releasing nucleic acid from a sample of the citrus plant, the environmental sample or the insect; (b) amplifying XF0324 and XAC1509 gene target nucleic acids using nucleic acid sequence based amplification (NASBA) with the amplification primers of SEQ ID NOS: 1 and 2, and SEQ ID NOS: 6 and 7, respectively, to generate a solution containing amplified single-stranded RNA amplification product(s) complementary to the target nucleic acid(s), if present in the nucleic acid from the sample; (c) detecting the presence of the RNA amplification product(s) in a lateral flow chromatographic device which uses nucleic acid sandwich hybridization, wherein, (i) a detectably-labeled detection oligonucleotide comprising SEQ ID NO: 4 is used to hybridize to a first sequence in an RNA amplification product corresponding to the XF0324 gene target, and a detectably-labeled detection oligonucleotide comprising SEQ ID NO: 9 is used to hybridize to a first sequence in an RNA amplification product corresponding to the XAC1509 gene target, and (ii) a capture oligonucleotide comprising SEQ ID NO: 3 is used to hybridize to a second sequence in an RNA amplification product corresponding to the XF0324 gene target, and a capture oligonucleotide comprising SEQ ID NO: 8 is used to hybridize to a second sequence in an RNA amplification product corresponding to the XAC1509 gene target, wherein the said capture oligonucleotides are discriminately immobilized on a detection membrane in the lateral flow chromatographic device to permit separate detection of the said RNA amplification products.

The foregoing *Xylella* and *Xanthomonas* assays, as well as the multiplex assay, may be Lateral Flow Microarray (LFM) assays, Semi-conductor Nanocrystal LFM (SN-LFM) assays, or other assay formats which incorporate nucleic acid sandwich hybridization, including but not limited to various lateral flow assay formats. In the case of *Xylella* assays, samples to be assayed may be any appropriate biological or environmental sample, including without limitation, foliar tissue, flower tissue, fruit tissue, xylem tissue, xylem fluid, insect tissue and insect fluid. In the case of *Xanthomonas* assays, samples to be assayed may be any appropriate biological or environmental sample, including without limitation, foliar tissues, flower and flowering tissues, fruit tissues, xylem tissues, xylem fluids, cankers, canker-like lesions, insect tissues and insect fluids.

The citrus pathogen assays of the invention couple a highly efficient isothermal amplification technique with LFM nucleic acid hybridization detection, thereby providing an inexpensive and facile means of rapidly detecting pathogen nucleic acid targets while circumventing hardware requirements for fluorescence detection and PCR thermocycling. In preferred embodiments, the citrus pathogen assays of the invention offer femtomole sensitivity, excellent linear dynamic range, and rapid and specific detection.

BRIEF DESCRIPTION OF THE DRAWINGS

FIG. 2. (A) LFM test designs were fabricated to allow characterization of the behavior of all capture and detection oligonucleotides designed for the detection of the Xf and Xac signatures described in Tables 1 and 2. These studies revealed specific hybridization behavior for of all but two of the candidates, XF2679 and XAC2743.

FIG. 6: Lateral flow sample preparation. TMV immunoassay strips (Agdia, Inc., Elkhart, Ind.) run using 200 µL of the indicated dilution of tobacco extract generated using 100 mg of dried tobacco in 3 ml extract buffer. (A) Dilutions of 1:200 and greater were negative by immuno-assay. (B) Reverse-transcriptase PCR (RT-PCR) was used to examine regions below, at and above the TMV capture zone (CZ). These reactions made use of previously reported primer sets for TMV detection (Jacobi, V., G. D. Bachand, et al., 1998, *Development of a multiplex immunocapture RT-PCR assay for detection and differentiation of tomato and tobacco mosaic tobamoviruses.* J Virol Methods 74(2): 167-78). Neat tobacco extract added directly to RT-PCR reactions was negative for TMV without prior immuno-capture to deplete inhibitors. Consistent with this interpretation, 1:50 dilutions of extract were positive by PCR presumably due to lower inhibitor concentrations (not shown). 200 µL of extract dilutions subjected to lateral flow immuno-capture resulted in positive detection at dilutions of up to 1:20,000. Significantly, neat extract generated positive PCR reactions only at and above the CZ while the region below the CZ was negative, presumably due to PCR inhibition. These data demonstrate that simple lateral flow immuno-capture without washes or further manipulation can alleviate PCR inhibition both through concentration of target particles and through physical sequestration of inhibitory matrix constituents. Significantly, the region above the CZ in the neat extract generates a positive PCR reaction apparently as a result of viral particle bleedthrough and a concomitant depletion of inhibitors.

DETAILED DESCRIPTION OF THE INVENTION

Unless otherwise defined, all terms of art, notations and other scientific terminology used herein are intended to have the meanings commonly understood by those of skill in the art to which this invention pertains, unless otherwise defined. In some cases, terms with commonly understood meanings are defined herein for clarity and/or for ready reference, and the inclusion of such definitions herein should not be construed to represent a substantial difference over what is generally understood in the art. The techniques and procedures described or referenced herein are generally well understood and commonly employed using conventional methodologies by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001). As appropriate, procedures involving the use of commercially available kits and reagents are generally carried out in accordance with manufacturer defined protocols and/or parameters unless otherwise noted.

Overview of Citrus Pathogen Assays

Figure 1A:
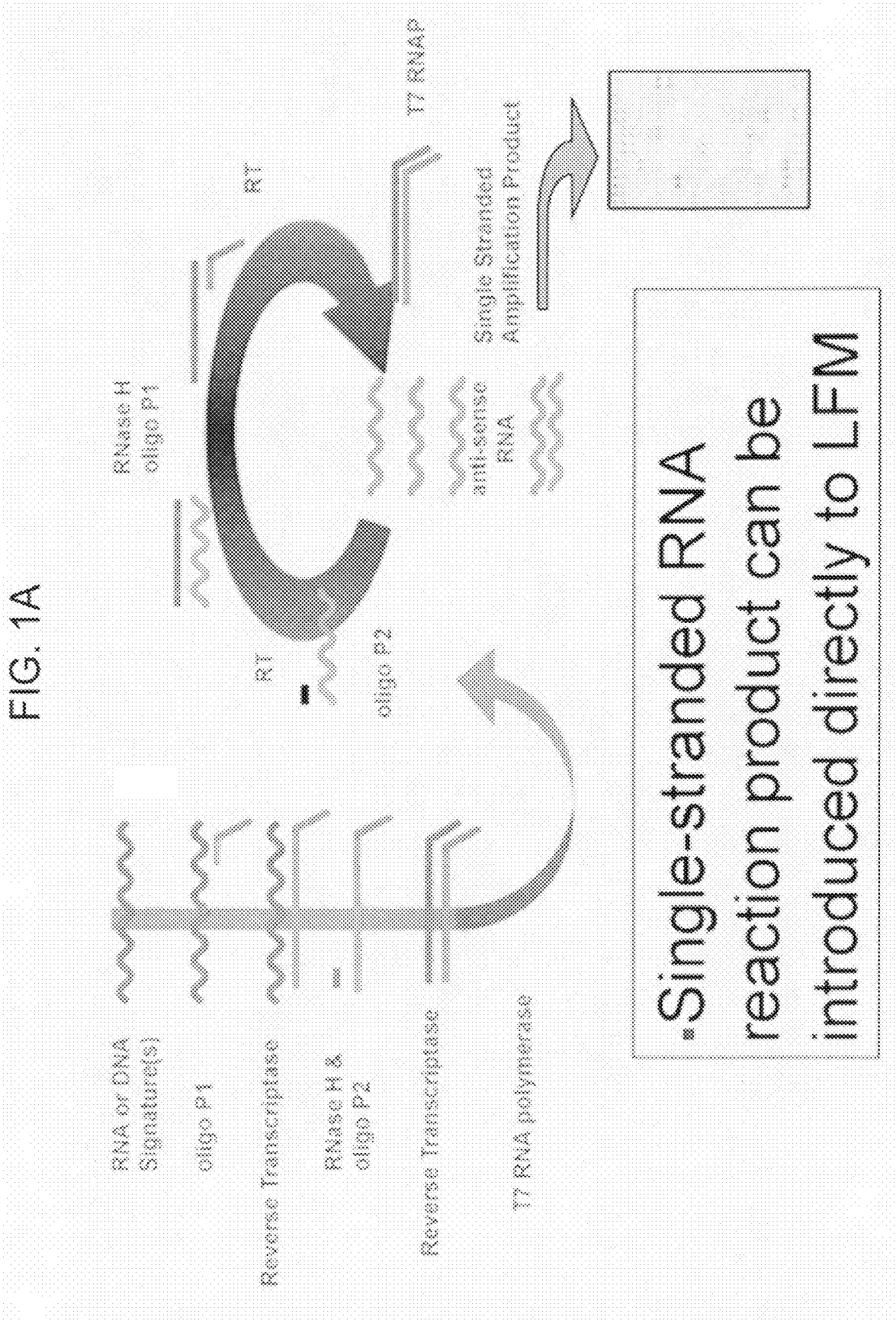
FIG. 1. (A) A schematic representation of the nucleic acid sequence-based amplification (NASBA) reaction. (B) Schematic representation of an exemplary LFM assay utilizing dyed-microsphere detection label. Capture probes are immobilized on lateral flow compatible membranes using a robotic positioning system and piezoelectrically actuated micro-pipettes. Dyed-microspheres, reversibly held on a conjugate release pad, are liberated into solution by the addition of sample (a nucleic acid amplification reaction). Detection oligonucleotides coupled to the dyed-microspheres, either by covalent cross-linking or a streptavidin/biotin interaction, hybridize to targets present in the sample. Hybridization of a non-overlapping region of the target to the LFM immobilized probes results in capture of target-microsphere complexes at cognate microarray feature positions and an increased local concentration of dyed-microsphere particles to form a visible colorimetric signal.

The invention provides rapid assays for the specific and sensitive detection of certain strains of *Xylella fastidiosa* and *Xanthomonas axonopodis* which cause citrus variegated chlorosis and citrus canker, respectively. The assays of the invention utilize a combination of isothermal amplification using NASBA and nucleic acid sandwich hybridization. Preferred embodiments combine NASBA amplification of target nucleic acids with lateral flow-based nucleic acid sandwich hybridization for capture and detection of amplified target. The assays of the invention may be practiced separately, or in a multiplexed format, allowing flexibility in overall assay design. Depicted in FIG. 1A is a schematic representation of a NASBA amplification scheme combined with LFM detection. FIG. 1B depicts a schematic representation of LFM using colorimetric label.

For the amplification component, the assays of the invention utilize the isothermal amplification methodology, NASBA (Compton, J., 1991, Nucleic acid sequence-based amplification. *Nature,* 350: 91-92; Kievits, et al., 1991, NASBA isothermal enzymatic in vitro nucleic acid amplification optimized for the diagnosis of HIV-1 infection. *J Virol Methods,* 35:273-286; Malek, et al., 1994, Nucleic acid sequence-based amplification (NASBA). *Methods Mol Biol,* 28: 253-260). In applicants' experience, NASBA-amplified target nucleic acids are detected at very high specificity in a matter of seconds in combination with LFM or SN-LFM detection platforms. NASBA is an RNA amplification methodology that offers several advantages over other RNA amplification methods, including the absence of a separate reverse transcriptase step. NASBA is also an isothermal reaction performed at 41° C., which obviates the need for a thermocycler and thus enables the citrus pathogen assays of the invention to be field-deployable, an important feature. A single-stranded antisense RNA product is produced during NASBA, which can be directly hybridized by a probe sequence to accelerate post-amplification interrogation of the product. Furthermore, the amplification power of NASBA has been reported to be comparable to, or sometimes even higher than that of PCR.

In preferred embodiments, NASBA primer sets which specifically amplify disease causing strains are employed. For the diagnosis of CVC, and the detection of CVC-causing *Xylella* bacteria, primer sets which specifically amplify a target sequence within the XF0324 gene of *Xylella fastidiosa* strain 9a5C (encoding periplasmic iron binding protein) are preferred. In a specific embodiment, the NASBA primers have the sequences of SEQ ID NOS: 1 and 2. For the diagnosis of CC, and the detection of CC-causing *Xanthomonas* bacteria, primer sets which specifically amplify a target sequence within the XAC1509 gene of *Xanthomonas axonopodis* pv *citri* strain (encoding a hypothetical protein) are preferred. In a specific embodiment, the NASBA primers have the sequences of SEQ ID NOS: 6 and 7. The foregoing two primer sets may also be used together in a single NASBA reaction to simultaneously amplify both the XF0324 and XAC1509 targets (see Example 3, infra).

As used herein, the terms "target sequence" and "target nucleic acid" are used interchangeably, and refer to a specific nucleotide sequence within a target nucleic acid molecule which is to be amplified and detected using the assays of the invention.

For the detection component, the assays of the invention utilize nucleic acid sandwich hybridization, employing sets of target-complementary oligonucleotides (or other nucleic acid molecules, such as dendrimers) to detect nucleic acid analytes. In the practice of the assay methods of the invention, nucleic acid target is detected redundantly, using (a) detectably labeled "detection" oligonucleotides complementary to one of two signature sequences on the target nucleic acid (i.e., oligonucleotides conjugated to a detectable label, such as dyed microspheres, semi-conductor nanocrystals, etc.), and (b) "capture" oligonucleotides complementary to the other signature sequence on the target, typically membrane-immobilized. In lateral flow assay format, the capture of amplified target nucleic acids by membrane-immobilized capture oligonucleotides and labeled detection oligonucleotides brings the label into contact with the membrane, displaying a visual or machine-readable optical signal. Thus, the assay requires positive hybridization to two distinct sequences on the target nucleic acid in order to produce a localized signal, resulting in very high assay specificity.

The detection oligonucleotide is labeled with a colorimetric, fluorescent or other detectable label, and is typically an oligonucleotide of about 20 or more bases which is complementary to a first sequence within the amplification product. Depending upon the particular assay format utilized, the detection oligonucleotide may be mixed together with the amplification reaction product, in solution, in order to generate a hybridization complex between the target amplification product and the detection oligonucleotide, or it may otherwise be made available for interaction and hybridization to the amplification product by, for example, embedding the detection oligonucleotide in a matrix (i.e., conjugate release pad) which is in lateral flow contact with both sample application and detection membrane components of a lateral flow test strip or device.

The hybridization complex between the detection oligonucleotide and the target amplification product may be applied to a test strip in solution, or allowed to flow via capillary action in formats in which the detection oligonucleotide is pre-embedded on the strip or device, to a lateral flow test strip detection membrane in which the capture oligonucleotide has been immobilized. The capture oligonucleotide is typically about 20 or more bases in length, is complementary to a second (and non-overlapping) sequence within the amplification product, and may be immobilized to a detection membrane, such as nitrocellulose, using methods well known in the art. In preferred LFM and SN-LFM assay format applications, the capture oligonucleotide is preferably deposited via a non-contact picoliter method, described further infra.

In preferred embodiments, detection and/or capture oligonucleotides may include a spacer of polyTs in order to provide improved hybridization kinetics, and may be designed to hybridize to target nucleic acid within 0, 1 or 2 bases of each other, in order to increase the stability of hybridization via the "base stacking" phenomenon (see further details, infra). Preferably, assays for the detection of CVC-causing *Xylella* bacteria and CC-causing *Xanthomonas* bacteria utilize capture-detection oligonucleotide pairs that are not only specific for the amplified target but also minimize any cross reactivity with the primer pairs used in the NASBA reaction, particularly where a multiplexed assay for the detection of both pathogens is implemented. In a specific embodiment, such capture detection oligonucleotide pairs comprise SEQ ID NO: 3 or nucleotides 16-37 thereof (capture), and SEQ ID NO: 4 or nucleotides 1-20 thereof (detection) for *Xylella fastidiosa* 9a5C; and, SEQ ID NO: 8 or nucleotides 16-35 thereof (capture) and SEQ ID NO: 9 or nucleotides 1-21 thereof (detection) for *Xanthomonas axonopodis* pv *citri* (see Examples 2 and 3, infra). Details concerning the design and construction of detection and capture oligonucleotides are presented in the subsection titled CAPTURE AND DETECTION OLIGONUCLEOTIDES, infra.

Assay Operation

In progression, the citrus pathogen assays of the invention initially involve extracting or releasing nucleic acid from a relevant sample (including without limitation a sample from citrus plant, a sample from an insect (vector) and an environmental sample), followed by NASBA-amplification of particular *Xylella* and *Xanthomonas* gene target nucleic acids, using primer sets specifically designed to amplify pathogen strains responsible for the diseases citrus canker and citrus variegated chlorosis. Appropriate plant samples for assay include without limitation samples of foliar tissues, flowering tissues, stem tissues, sap, xylem tissue, xylem and the like. Insect samples may include insect tissue, such as abdomen tissue samples, and samples from interior cavities, including various fluid samples. Additionally, the assays of the invention may find use in testing samples of soil, water, particulates filtered from air and particulates washed from leaf surfaces. Such environmental sample tests may enable studies designed to identify the natural reservoirs of these pathogens.

Extracted nucleic acids may be purified prior to amplification. A number of column type DNA purification devices are commercially available and may be employed for this purpose. Various other techniques for purifying DNA may be employed, including without limitation, chromatographic methods, electrophoresis, gradient separation, affinity purification, etc.

Following amplification using NASBA, a single-stranded RNA amplification product is produced, which is then detected by nucleic acid sandwich hybridization, typically in a lateral flow chromatographic device or test strip, such as an LFM or SN-LFM device or test strip.

In some embodiments of the assays of the invention, sample preparation is achieved using lateral flow methodologies, such as those described under the subsection titled LATERAL FLOW-BASED NUCLEIC ACID SAMPLE PREPARATION, infra. This technology adds an up-front, nucleic acid extraction module that can be used in combination with a detection test strip or device, or engineered to be in lateral flow contact with the detection module of a lateral flow test strip or device. The sample preparation module may also incorporate NASBA amplification, on-board, so that all aspects from tissue sample to answer are housed in an integrated assay format.

In another, related aspect of the invention, methods for diagnosing citrus canker and/or citrus variegated chlorosis are provided, and comprise carrying out the *Xylella fastidiosa* 9a5c strain and *Xanthomonas axonopodis* pv *citri* assays of the invention. The presence of these particular strains provides an indication of the presence or emergence of these plant diseases.

For illustration purposes, in lateral flow formatted assays, a solution containing one or more target sequences to be detected (generated, i.e., by NASBA amplification on extracted nucleic acid from a relevant sample) is introduced to a sample pad or other sample receiving zone. This may be achieved by dipping the lateral flow device sample pad/sample receiving zone into the solution, or by dropping a quantity of the solution onto the sample pad/sample receiving zone of the lateral flow device. When utilizing LFM devices, the composition of the buffer solution carrying the target sequence(s) is not critical; however, several practical considerations are taken into account to assure compatibility of the buffer with the device. Most significantly, the ionic strength of the sample buffer must be such that precipitation or aggregation of the detection particles does not occur. Similarly, sufficient ionic strength of the buffer is required to support hybridization during lateral flow. Impregnation of the sample pad and/or a conjugate release pad (containing labeled detection oligonucleotide) with Triton-X100, SDS, BSA, ficol, and/or polyvinyl pyrolidone, or introduction of these components to the sample buffer itself, can stabilize the detection particles and block non-specific interactions between the detection particles and the detection membrane. While a range of concentrations of these reagents can be used successfully, buffers of proven efficacy include 0.1% ficol, 0.1% BSA, 1% Triton X-100, and 150 mM NaCl. This particular buffer supports mono-disperse detection particle suspensions.

Additionally, buffers containing higher concentrations of Triton X-100 and SDS have been found to support higher ionic strength environments without detection particle aggregation and may be used to facilitate hybridization. For example, 3% Triton X-100, 0.1% SDS, 600 mM NaCl has been shown to support subnanomolar hybridization-based detection on the device.

Once on the sample pad/sample receiving zone, the analyte solution flows from the proximal (sample) end towards the distal (detection) end of the device. In one embodiment, detection oligonucleotide-functionalized dyed microbeads are embedded into the conjugate release pad component of the device, preferably in lyophilized form, ready to be rehydrated as the analyte solution travels into this area of the device. As the analyte solution moves across the conjugate release pad, the microbeads are rehydrated and are available for detection oligonucleotide hybridization to target sequences within the sample. Target sequences, when present, will become hybridized to the detection oligonucleotide and thus to the beads. This complex continues lateral flow migration to the detection membrane, where immobilized capture oligonucleotides hybridize to the target sequence, thus capturing the target sequence-bead complex.

LFM and SN-LFM Assay Platforms

In preferred embodiments of the invention, the citrus pathogen assays are formatted for lateral flow detection, even more preferably formatted for lateral flow microarray detection (LFM) or Semi-conductor nanocrystal LFM (SN-LFM). LFM is a recently described technology which miniaturizes lateral flow nucleic acid detection, and provides several distinct advantages in the context of field-deployable nucleic acid assay design, including reduced reagent use, femtomole sensitivity, excellent linear dynamic range, no specialized equipment requirements and rapid detection kinetics (Carter and Cary, 2007, Nucl. Acids Res. 1-11, doi:10.1093/nar/gkm2690). LFM is more fully described in co-owned, co-pending U.S. patent application Ser. No. 11/894,910, filed Aug. 27, 2007. SN-LFM is an improved LFM utilizing semiconductor nanocrystal labels for greater assay performance (i.e., increased sensitivity and linear dynamic range) and is described in co-owned, co-pending U.S. Provisional Patent Application No. 61/126,640 Filed May 5, 2008.

LFM platforms are capable of utilizing either colorimetric detection modalities, such as is enabled by the use of dyed polystyrene microspheres and the like, or by fluorescent nanoparticle detection modalities, such as is enabled by semiconductor nanoparticles, quantum dots and the like (SN-LFM).

Lateral flow chromatographic devices employing nucleic acid sandwich hybridization typically comprise a series of absorbent substrates which are used to transport analyte in a lateral manner to components containing certain reagents or materials required for the detection of the analyte. For example, such a lateral flow chromatographic device may comprise, (a) a sample receiving zone for receiving an aliquot of the sample and for receiving a labeled detection oligonucleotide, which detection oligonucleotide comprises a sequence which is complementary to a first sequence of the target nucleic acid; and, (b) a capture zone in lateral flow contact with the sample receiving zone, said capture zone comprising a microporous membrane, onto which at least one capture oligonucleotide is immobilized and which comprises a sequence which is complementary to a second sequence of the target nucleic acid. In an alternative design, a labeling zone in lateral flow contact with said sample receiving zone is inserted up-stream of the capture zone and is in lateral flow contact with the capture zone. A labeling zone comprises a porous material containing at least one detection oligonucleotide reversibly bound thereto, which detection oligonucleotide is complementary to a first sequence of the target nucleic acid and is coupled to a detectable label, thereby enabling the label step to take place on the device.

In a simplified illustration, one type of LFM device that may be used to execute the assays of the invention is structurally organized into at least 3 zones, comprising in linear orientation, (a) a sample pad constructed from absorbent material onto which a liquid, nucleic acid-containing sample is deposited (i.e., NASBA reaction), (b) a conjugate release pad containing a least one oligonucleotide-fitted detection particle (e.g., microsphere, bead, quantum dot), and (c) a detection zone comprising a nitrocellulose or nylon membrane containing at least one immobilized capture oligonucleotide. In some designs, an absorbent material which is capable of facilitating the lateral flow of the liquid sample from the sample pad end of the device to and through the detection zone is included. In some designs, the sample pad (a) and the conjugate release pad (b) are combined. In still other designs, the conjugate release pad element is eliminated, and the sample to be assayed for the presence of a target nucleic acid is mixed with the oligonucleotide-fitted detection particle prior to placing the sample onto the sample pad.

The first substrate, or sample pad or sample receiving zone, comprises an absorbent material preferably composed of a matrix, with minimal nucleic acid binding properties, that will permit unobstructed migration of the nucleic acid analyte to subsequent stages of the apparatus without depletion. In a preferred design, the sample pad is composed of a cellulose fiber pad such as Millipore cellulose fiber sample pad material (Cat# CFSP223000). In cases where separate sample and conjugate release pads are employed in the LFM device, the sample pad is situated within the device such that it is in physical (or, lateral flow) contact with the conjugate release pad.

The substrate which contains the labeled detection oligonucleotide conjugate is referred to as the conjugate release pad or labeling zone. In some designs, the labeling zone is also used to receive sample directly. The conjugate release pad comprises a matrix composed of a material with minimal nucleic acid binding capacity and of a physical composition which allows dried detection particles to be liberated into solution with minimal residual binding to the matrix. Examples of materials suitable for conjugate pads include glass fiber and polyester materials (e.g., rayon).

These materials are commonly available from various commercial sources (e.g., Millipore, Schleicher & Schuell).

The detection membrane of the capture zone may be any microporous membrane material which is lateral flow compatible, typically microporous cellulose or cellulose-derived materials such as nitrocellulose (e.g., HiFlow 135, Millipore)

or nylon. In some formats, the sample receiving zone and the capture zone comprise a contiguous microporous membrane.

Optimally, the microporous membrane of an LFM device defines a relatively narrow flow path. This may be achieved, for example, by utilizing narrow strips of microporous membrane material. Excellent results have been obtained with membrane strips of 5 mm or less in width, with the best results being obtained with strips of 3 mm or less (see U.S. patent application Ser. No. 11/894,910, filed Aug. 27, 2007. As will be appreciated, other means for retaining a narrow flow path of less than 5 mm or less than mm may be used, and may include without limitation the use of barriers which define borders which limit the flow path to a channel.

The microporous membrane of the capture zone is a lateral flow compatible membrane such as cellulose, nitrocellulose, polyethersulfone, polyvinylidine fluoride, nylon, charge-modified nylon, and polytetrafluoroethylene. Typically, the membrane is nitrocellulose. The detection membrane is typically provided with a backing material for support, such as mylar or similar plastic materials. The membrane may be treated with agents that inhibit non-specific binding of analyte or other reagents used in an LFM assay.

In utilizing nitrocellulose, pore sizes typically range between 0.2 and 20 µm, and more typically between 0.2 and 12 µm. In preferred LFMs utilizing particle labels, the pore size of the microporous membrane should be on the order to about 10 times the diameter of the particle.

In preferred LFM designs, the detection membrane is composed of a supported nitrocellulose membrane of sufficiently large pore structure to allow the unimpeded transport of detection reagent through the membrane matrix. Examples of suitable nitrocellulose materials for dyed microsphere mediated detection are Millipore HiFlow Plus HF90, HF135, Schleicher & Schuell Prima 60, Schleicher & Schuell Prima 85. The Millipore HF13504 nitrocellulose membrane has been demonstrated to provide rapid, specific and sensitive detection when patterned with appropriate capture oligonucleotides. The microporous membrane is placed in lateral flow contact with the labeling zone (conjugate release pad).

Materials suitable for use as an absorbent pad include any absorbent material, including, but not limited to, nitrocellulose, cellulose esters, glass (e.g., borosilicate glass fiber), polyethersulfone, cotton, dehydrated polyacrylamide, silica gel, and polyethylene glycols. The rate of capillary flow can be controlled by choosing the appropriate absorbent zone material.

LFM formatted assays of the invention may be encased in a housing as described in, e.g., U.S. Pat. No. 5,451,504. Materials for use in the housing include, but are not limited to, transparent tape, plastic film, plastic, glass, metal and the like. Such housings preferably contain an opening or sample port for introducing sample, as well as a window(s) permitting the visualization of the detection zone(s) of the detection membrane.

Microarray Fabrication

In the fabrication of an LFM device, the microporous membrane of the capture zone is used for patterning capture oligonucleotides. In preferred fabrications, capture oligonucleotides are patterned onto the detection membrane or substrate (i.e., nitrocellulose) with spot diameter sizes ("feature sizes") of about 1 mm or less, preferably 600 µm or less, more preferably less than about 300 µm diameter, and in some embodiments, smaller (i.e., 50 to 200 µm, 50 to 250 µm, 50 to 300 µm). Oligonucleotide concentrations for spotting are generally in the range of 200 µM-800 µM. In embodiments in which PNAs or LNAs are used to synthesize oligonucleotides, lower concentrations may suffice.

Detection membranes may be patterned to suit the desired design of the detection element of the device. Methods for depositing nucleic acids and proteins onto microporous membranes such as nitrocellulose are well known, and negative and positive control reagents as well as capture reagents may be patterned on to the detection membrane using any of a number of deposition techniques. These techniques can be selected based on the density of information to be represented on the detection membrane. Manual deposition by pipette, automated deposition by robotics through contact mediated processes (stainless steel pins on a contact microarray printing robot) or noncontact mediated processes such as piezo responsive micropipettes, may all be used to fabricate suitable LFM devices for carrying out the assays of the invention. Preferably, when using nitrocellulose and similar membranes, non-contact printing techniques are used to deposit capture oligonucleotides onto the detection membrane, in order to retain the structural integrity of the detection membrane material.

Additionally, more convention means may be employed, including various techniques commonly used to fabricate hand held assay devices for the immunological detection of proteinaceous analytes in the context of a lateral flow immunochromatographic device. For example, immobilization of capture oligonucleotides directly on the detection membrane may be accomplished by using high salt to adsorb the nucleic acid molecules to the surface of the membrane, combined with baking at about 80° C. to permanently fix the adsorbed oligonucleotides. Additionally, oligonucleotides may be deposited onto the membrane (i.e., nitrocellulose), air dried, and subjected to UV radiation (see Examples herein). Capture oligonucleotides may also be fixed directly to detection membrane by vacuum transfer in the presence of an equimolar concentration of sodium chloride and sodium citrate, or by the use of ultraviolet irradiation. The capture oligonucleotides may also be covalently linked to charge-modified nylon. The capture oligonucleotide may also be coupled to a particle such as a latex or polystyrene microsphere and then immobilized by deposition of the oligonucleotide-carrying particle into the pores of a porous substrate such as nitrocellulose or nylon. In other embodiments, capture oligonucleotides may incorporate a reactive ligand (e.g., biotin) and may be immobilized indirectly on the detection membrane as a result of the interaction between the ligand and an immobilized member of a binding pair (e.g., streptavidin).

Detection membranes may be patterned with positive and negative control reagents and capture reagents in an array such that the physical position of each reagent is known. Positive control reagents can be composed of oligonucleotides complementary to detection oligonucleotides immobilized on detection reagents (i.e. dyed microspheres linked to oligonucleotides through a covalent bond or through an affinity interaction such as that mediated by streptavidin/biotin interactions). Alternatively, in embodiments where the streptavidin/biotin interaction is used to couple dyed microspheres to oligonucleotides the positive control array element can be composed of biotin in any of a number of forms suitable for immobilization on nitrocellulose (for example, a biotin labeled nucleic acid). Following binding to detection oligonucleotides, free biotin binding sites on streptavidin-conjugated dyed microspheres remain available for interaction with immobilized biotin on the detection membrane, thus providing one form of positive control.

Another positive control may be achieved by the immobilization of oligonucleotide on the detection membrane. The use of an oligonucleotide complementary to the dyed microsphere-conjugated detection oligonucleotide as a positive control allows direct hybridization of the detection oligonucleotide/dyed microsphere complex following lateral flow chromatography over the positive control. Negative controls for hybridization specificity can be incorporated into the device by patterning the detection membrane with detection oligonucleotide or other nucleic acid sequences predicted, by means known to those skilled in the art, to not hybridize to the detection oligonucleotide sequence.

For nucleic acid analytes, capture reagents are composed of oligonucleotides synthesized such that the sequence is complementary to a region of the analyte target nucleic acid not overlapping with the region complementary to the detection oligonucleotide. Ideally, the predicted secondary structure of the analyte target nucleic acid is examined to identify those regions exhibiting reduced likelihood of participating in intramolecular hydrogen bonds. Such regions are preferable sites for detection and capture oligonucleotide binding.

Array elements may take the form of lines, stripes, dots or human readable icons, letters or other forms or shapes deemed useful to the interpretation of device read-out. In the case of spots or dots deposited by robotic or manual means, individual feature sizes from 50 microns to 5 mm have been shown to provide accurate and interpretable hybridization mediated detection of 20 fmol analyte DNA molecules. See, as an example, FIG. 5.

The LFM formatted assays of the invention can make use of diverse detection modalities, including visual detection signals resulting from the capture and increased local concentration of an appropriate detection particle. The resulting colorimetric signal can be visualized by eye. Alternatively, for more quantitative and sensitive detection of signal, an electronic instrument capable of detecting colorimetric signals may be employed. Such instruments include standard flatbed scanners, dedicated lateral flow chromatographic strip readers (e.g. QuadScan, KGW Enterprises, Inc), or a simple CCD based devices fabricated for the detection of colorimetric signals such as those employed by commercially available immunochromatographic test strips (e.g. Clearblue Easy Digital Pregnancy Test).

Embodiments that employ fluorescent detection reagents such as fluorescent nanoparticles (e.g. Qdots, QuantumDots, Inc.) may be read using any of a number of ultraviolet light sources including hand held UV lamps, UV emitting LEDs, and light sources with sufficient emission in the UV to excite the nanoparticles. A simple filter can be used to enhance the visualization of nanoparticle fluorescence emissions. For example, a long pass filter with a cut off below the emission wavelength of a nanoparticle label may be employed. In the case of excitation with a white light source, an additional filter to limit excitation to UVA and shorter wavelengths can be used (e.g., a 380 nm short pass filter).

A low cost and highly simplified signal acquisition system for use in conjunction with SN-LFM is described in co-owned, co-pending U.S. Provisional Patent Application 61/126,640, filed May 5, 2008. This device utilizes a low voltage, long wave length UV excitation system based on LED technology. CCD or CMOS imaging is used to provide sufficient signal-to-noise, sensitivity, and bit depth (dynamic range) to allow semi-quantitative analysis of SN-LFM hybridization events. Image is communicated via standard USB interface to a PC, hand-held computer, smart phone, or similar data processing instrument.

Capture and Detection Oligonucleotides

The assays of the invention incorporate two classes of oligonucleotide referred to here as "detection" and "capture" oligonucleotides. The detection oligonucleotide is conjugated to a detectable label (i.e., polystyrene microsphere, semiconductor nanocrystal, etc) that when concentrated by capture through hybridization, renders the capture zone optically distinguishable from the surrounding substrate and from additional capture zones where the detection reagent has not been sequestered.

In some embodiments, a nucleic acid complex, such as a DNA dendrimer or branched-DNA molecule, carrying multiple detectable moieties, such as fluorescent molecules or biotin, can be used to amplify lateral flow microarray signal intensity. By generating DNA dendrimers carrying a detection sequence complementary to a region of the target (detection sequence) each hybridization event at the capture zone results in the localization of multiple detectable labels. For example, using a highly biotinylated dendrimer and streptavidin coated semi-conductor nanocrystals, fluorescent signal amplification can be realized. The large number of streptavidin binding sites on biotinylated dendrimers will increase the number of streptavidin bound nanocrystals captured by each hybridization event and generate a correspondingly amplified signal. Several potential advantages, especially with respect to multiplexed detection, may be realized using this approach. Specifically, the use of a generic biotin/streptavidin interaction allows the simultaneous use of multiple detection probe sequences without requiring the preparation of multiple nanocrystal-detection probe conjugates. Together with the use of generic tag sequences added to amplicons through the use of specially designed NASBA primers, this approach is compatible with the development of generic tag-based SN-LFMs suitable for the detection of differing panels of pathogens without redesign of the overall layout.

The detection oligonucleotide is designed such that the melting temperature of the resulting oligonucleotide allows hybridization to its cognate sequence on the analyte under ambient conditions with sufficient rapidity to allow duplex formation to occur during lateral flow. Detection oligonucleotides with Tm of 50-70° C. have been shown to provide effective reagents for the detection of relevant analytes (using approximately 20-mer oligonucleotides).

Detection oligonucleotides are synthesized with suitable modifications to allow the efficient linkage to appropriate detection reagent. In some embodiments it is advantageous to include a spacer sequence consisting of 9 to 20 T residues proximal to the modified end of the oligonucleotide that will be coupled to the detection reagent (see, i.e., Examples 2 and 3, infra). Chemistries of known suitability for use in the device include biotin/streptavidin through a biotin incorporated onto either the 5' or 3' end of the detection oligonucleotide and covalent cross-linking through a primary amine incorporated into either the 3' of 5' end of the detection oligonucleotide. In one preferred process, detection oligonucleotides are covalently linked to polystyrene microspheres using the coupling agent 1-etyl-3-(3-dimethylaminopropyl-diimide HCl (EDAC). Other methods that mediate the formation of a stable complex between the detection reagent and the detection oligonucleotide under assay conditions should also be suitable for use in the fabrication of the device.

The second class of oligonucleotide used in the device is the capture oligonucleotide. This reagent is immobilized on the microporous detection membrane through the use of standard methods for coupling nucleic acids to nitrocellulose or nylon, including without limitation drying followed by ultraviolet light cross-linking using 5000 microjoules UV. The capture oligonucleotide is designed such that the sequence is complementary to the analyte target nucleic acid at a region predicted to have little or no secondary structure. The length of the capture oligonucleotide is typically approximately 20 bases in length or of a length to generate a predicted melting temperature of approximately 50-70° C. In some embodiments it may be advantageous to add a spacer sequence consisting of 9 to 20 T residues (see, i.e., Examples 2 and 3, infra).

Detection and capture oligonucleotides can be synthesized using well known DNA synthesis chemistries. The incorporation of modified nucleic acids such as PNA (peptide nucleic acid) or LNA (locked nucleic acid) may be useful for the enhanced hybridization properties of these DNA derivatives. The use of PNA or LNA moieties in the preparation of detection and/or capture oligonucleotides will be useful in manipulating the desired melting temperature, and so may allow shorter oligonucleotides to be employed for detection and/or capture where sequence constraints preclude longer DNA oligonucleotides.

In some embodiments, detection and capture oligonucleotides are designed to hybridize to target nucleic acid within 0, 1 or 2 bases of each other, in order to increase the stability of hybridization via the "base stacking" phenomenon. Base stacking has been reported to stabilize hybridization and allow efficient capture of dilute nucleic acids by hybridization.

Lateral Flow Sample Preparation Methods and Systems

The assays of the invention may also take advantage of highly simplified lateral flow chromatographic nucleic acid sample preparation methods, devices, and integrated systems for the efficient concentration of trace samples and the removal of nucleic acid amplification inhibitors. Such methods and devices are described in co-owned, co-pending U.S. Provisional Patent Application No. 61/126,645, filed May 5, 2008. In one illustrative embodiment, a fully integrated assay for detecting CVC-causing *Xylella* and/or CC-causing *Xanthomonas* is provided, and functionally comprises lateral flow immuno-capture of *Xylella* and/or *Xanthomonas* bacteria, lysis directly within the lateral flow matrix, target amplification by NASBA, and detection using sandwich hybridization, all in a lateral flow format. Alternatively, a sample preparation module may be employed, followed by transfer of the processed sample to another module of the assays (i.e., NASBA module, LFM detection module).

For example, such a sample preparation module may comprise a sample receiving zone for receiving an aliquot of a fluid sample derived from a citrus plant to be tested for CVC and/or CC causing pathogens, together with an immuno-capture zone in lateral flow contact with said sample receiving zone, which contains immobilized antibody that is reactive with one or more bacterial surface antigens. Such a module may be used to capture *Xylella* and/or *Xanthomonas* cells, and may also contain means for lysing the bacteria, and for amplifying the nucleic acid liberated therefrom. The module may be coupled to or integrated with a sandwich hybridization detection module. Once immobilized by the immuno-capture zone, the bacterial cells may be subsequently washed, lysed and any liberated nucleic acids amplified.

Immuno-capture zones may be prepared, for example, as follows. Antibody solutions are prepared in a physiological ionic strength buffer at a concentration found empirically to provide specific binding to the antigen (typically 0.01 mg/ml to 1 mg/ml). Antibody deposition onto a large pore nitrocellulose membrane can be accomplished by any of a number of means including but not limited to manual application, airbrush deposition, robotic fluid handling systems or similar methods that deposit controlled and reproducible volumes of ligand onto the substrate. Suitable substrates include HiFLow 135 (Millipore, Inc) and similar products available from a variety of commercial providers. Once deposited onto the substrate the ligand is immobilized by drying (in the case of proteinaceous ligands) and/or by UV irradiation at a dose of 5000 microjoules (in the case of nucleic acid/LNA immobilization).

This aspect of the invention is exemplified by the successful sequestration of TMV particles from crude macerated dried tobacco leaf by immuno-affinity chromatography within a nitrocellulose membrane context, as described in Example 4, infra. The samples utilized in the experiments described in Example 4 represent a very challenging matrix owing to the presence of complex polysaccharides, organic mater and other constituents strongly inhibitory to enzymatic manipulations, such as PCR and NASBA amplification, as well as potentially confounding non-probative nucleic acids (plant derived DNA and RNA). Therefore, it may be desirable to utilize a preceding lateral flow mediated immuno-capture step in the analysis of samples to be tested with the assays of the invention, particularly where the target analyte (i.e., a particular gene of CVC-causing *Xylella* or CC-causing *Xanthomonas*) is a minority species and NASBA inhibitors are present that preclude direct amplification of the target without preparatory processing.

Disease-Transmitting Vector Infection Assays

In yet another aspect, the invention's citrus assays may be used to monitor various insects for the presence of CVC-causing *Xylella* and/or CC-causing *Xanthomonas* bacteria. CVC is known to be transmitted by certain insect vectors, including sharpshooter leafhoppers and spittlebugs (see BACKGROUND, supra). Accordingly the invention's *Xylella* assay may be used to detect and monitor the presence of citrus variegated chlorosis-causing *Xylella fastidiosa* strains in known insect vector populations, as well as to identify potentially new insect vectors capable of transmitting CVC. In this regard, a typical sample matrix would comprise tissue or fluids taken from an appropriate insect vector.

Although CC is not known to be transmitted by any particular vector, the *Xanthomonas* assay of the invention may be used to test for the presence of CC-causing *Xanthomonas* in insects which might be considered vector candidates, and therefore may be useful in identifying vectors and in the management of citrus canker.

EXAMPLES

Example 1

Identification of Candidate Target Sequences for *Xylella* and *Xanthomonas*

Comparative Sequence Analysis:

Bioinformatics analysis of available genome sequences for *Xylella* and *Xanthomonas* species of interest and their nearest phylogenetic neighbors was conducted in order to identify candidate nucleic acid signatures for the development of strain specific detection assays for *Xylella fastidiosa* strain 9a5c and *Xanthomonas axonopodis* pv *citri*.

Target Candidates:

Based on favorable predicted melting temperatures and low secondary structure potentials within regions of interest, putative signatures (targets) were identified for further study. This effort identified six *X. fastidiosa* strain 9a5c candidate signatures and five *X. axonopodis* pv *citri* candidate signatures for further evaluation. For each candidate signature, NASBA primers were computationally designed, and the regions homologous to the pathogen derived target sequence are shown in Tables I and II.

TABLE I

CANDIDATE *XYLELLA* TARGET SEQUENCES

| Gene id | length | definition | primer 1 | primer 2 |
|---|---|---|---|---|
| XF0324 | 134 | periplasmic iron-binding protein | CGAAGCACTCACTTCTTCATAGGTC (SEQ ID NO: 10) | CCATTTTATGGTGTGGGCG (SEQ ID NO: 11) |
| XF1614 | 180 | penicillin binding protein | TCTGTGTTCCGTCAGTCATAAGAAT (SEQ ID NO: 12) | GCAGTCTGGTTGCGTTAACTGTA (SEQ ID NO: 13) |
| XF2288 | 170 | phage-related intergrase | GGTCAATCACTTTCCCTAACTCTGT (SEQ ID NO: 14) | GATGGATTTAGCCTATTTAACCGG (SEQ ID NO: 15) |
| XF2679 | 164 | virulence protein | TCAAGTTGAGATCCACAAGAACTGT (SEQ ID NO: 16) | TTCCATTTGCGCCAAGATAG (SEQ ID NO: 17) |
| XF1491 | 189 | hypothetical protein | TGTGTACAACATATCGCATATCCAG (SEQ ID NO: 18) | GTATCTGCAAGTGCTCAATTCCA (SEQ ID NO: 19) |
| XF1877 | 181 | hypothetical protein | TGATAAGCATTAATAGGAGCGATC (SEQ ID NO: 20) | GTGGTTTGATTAATGGGGCAG (SEQ ID NO: 21) |

TABLE II

CANDIDATE *XANTHOMONAS* TARGET SEQUENCES

| | | | | |
|---|---|---|---|---|
| XAC0089 | 161 | abortive infection phage resistance protein | TGCTCGTATCTTCAAGTAAATTGGC (SEQ ID NO: 22) | GGACACCATACTTGAAGCCGTTA (SEQ ID NO: 23) |
| XAC2743 | 158 | Oar protein | TGAATGTGTTCAATGTACTGAACGA (SEQ ID NO: 24) | GAAATCGTATGACGCAGTTAGGC (SEQ ID NO: 25) |
| XAC3534 | 154 | general secretion pathway protein D | GGAGTACCATTCCTCAGTAAGTTGC (SEQ ID NO: 26) | TCTTGGCGTATTCATCCGTC (SEQ ID NO: 27) |
| XAC4209 | 157 | colicin V secretion ABC transporter ATP-binding protein | GTGGCTGAAGATATTAATGACCCAC (SEQ ID NO: 28) | GATCTCAGAGTCCAACGGCAA (SEQ ID NO: 29) |
| XAC1509 | 159 | hypothetical protein | GGGTCACAACCTGAGAAATCTCTAT (SEQ ID NO: 30) | TTTTGAGTGCGCGTTGCTA (SEQ ID NO: 31) |

Example 2

Initial Screening of Candidate Target Sequences

The candidate *Xylella* and *Xanthomonas* signatures identified in Example 1, supra, were screened for suitability in an LFM assay paradigm.

To screen candidate signature sequences for favorable behavior in lateral flow detection schemes, capture and detection probes were generated for all candidate signatures shown in Tables 1 and 2. The resulting oligonucleotides were deposited onto large pore nitrocellulose substrates for LFM device fabrication (FIG. 2A). The resulting LFMs were then used to screen oligonucleotide sequences for specific hybridization under standard LFM running conditions (FIGS. 2B, C).

These studies identified only two candidate capture/detection probe pairs exhibiting unfavorable cross hybridization to other candidates. They are XF2679 and XAC2743. XF0324 and XAC1509 based probes exhibited no detectable cross hybridization to each other or to other probe candidates. XF0324 and XAC1509 were therefore subjected to more rigorous characterization studies (see, Example 3). The nucleotide sequences of preferred capture and detection probes designed to assay for these *Xylella* and *Xanthomonas* signatures are shown in SEQ ID NOS: 3-4 and 8-9, respectively, in the Table of Sequences, infra.

Example 3

LFM Assay Detection of *Xylella* XF0324 and *Xanthomonas* XAC1509 Signatures To establish the relative assay sensitivity afforded by the initial capture and detection oligonucleotides designed (Example 2), LFM assays for the detection of *Xylella* and *Xanthomonas* targets were conducted using synthetic oligonucleotide targets designed to carry the predicted sequence of signature/target amplicons.

Materials and Methods:

Synthetic RNA Targets for *Xylella* and *Xanthomonas* Targets:

To test NASBA primer designs and to define the amount of template required to obtain LFM-based detection following amplification, a test system was designed, based on a pUC57 vector carrying the XF0324 or XAC1509 signature/target sequences in front of a T7 RNA polymerase promoter. These constructs were used to program in vitro transcription reactions and the resulting RNA products purified and quantified. Dilution series experiments were conducted to define the limit of detection with respect to the amount of in vitro synthesized target. As little as 0.2 attograms, corresponding to approximately 1 copy, of purified XF0324 or XAC1509 transcript generated by in vitro transcription were amplified by NASBA for subsequent detection by hybridization sandwich assay.

LFM Fabrication: Lateral flow microarrays (LFMs) were printed using a NanoPlotter 2.0 (GeSim, mbH, Dresden, Germany) non-contact picoliter deposition system equipped with NanoTips (GeSim). Unless otherwise indicated, LFMs were patterned with 400 µM solutions of oligonucleotide in $H_2O$ containing a 1:50 dilution of Ponceau S (P7767, Sigma) as a tracking dye. A lateral flow compatible nitrocellulose membrane (HiFlow 135, Millipore) was used as the LFM substrate. Following oligonucleotide deposition, nitrocellulose membranes were air dried and exposed to 5000 µJ UV in a StrataLinker (Stratagene). The resulting membrane sheets were cut into 3 mm wide, 30 mm long strips which were either used directly with buffer suspended dyed microspheres or assembled with conjugate release pads into a custom plastic housing. Housings were fabricated from polycarbonate sheet cut using a $CO_2$ laser (VersaLaser VL-300, Universal Laser Systems, Inc., Scottsdale, Ariz., USA). Conjugate release pads were made by impregnating glass fiber conjugate pad (GFCP203000, Millipore) with dyed microspheres covalently conjugated to Xf or Xac detection probes sequences [SEQ ID NOS: 4 and 9 respectively] in 1% SDS.

Microsphere saturated release pads were allowed to air dry under ambient conditions prior to assembly with LFM membranes.

Capture and Detection Oligonucleotides: Capture and detection oligonucleotide sequences for *Xylella* and *Xanthomonas* targets were as follows:

```
Xylella LFM Oligonucleotide Hybridization Probes:
CAPTURE PROBE (SEQ ID NO: 3):
5' NH2-ttt ttt ttt ttt ttt GGTGATTGCTGAT-
TACCAGCGC 3'

DETECTION PROBE (SEQ ID NO: 4):
5' TTGCATCCTGGAACTAAAGT ttt ttt ttt ttt ttt-NH2 3'

Xanthomonas LFM Oligonucleotide Hybridization
Probes:
CAPTURE PROBE (SEQ ID NO: 8):
5' NH2-ttt ttt ttt ttt ttt ATGTGGCCCTATCGCCATCG 3'

DETECTION PROBE (SEQ ID NO: 9):
5' GTTGATTCCATCCTCAGAGAC ttt ttt ttt ttt ttt-NH2 3'
```

Amine modifications and $T_{15}$ spacer sequences were included on the 5' ends of the detection oligonucleotides to allow covalent cross-linking to dyed microspheres and to facilitate hybridization in LFMs. Similarly, $T_{15}$ spacer sequences were included in the capture probes to facilitate hybridization.

Conjugation of Detection Oligonucleotides to Dyed Microspheres: SPHERO™ carboxyl-polystyrene 0.35 µm blue microspheres (Spherotech) were covalently conjugated to amino modified oligonucleotide detection probes using the coupling agent 1-etyl-3-(3-dimethylaminopropyl-diimide HCl (EDAC, Pierce) under conditions adapted from Spiro et al (Spiro et al., 2000, *A bead-based method for multiplexed identification and quantitation of DNA sequences using flow cytometry*. Appl Environ Microbiol 66(10): 4258-65). Briefly, $4 \times 10^{10}$ microspheres were suspended in 100 mM 2-(N-morpholino)ethanesulfonic acid pH 4.5 (MES, Sigma). Indicated amounts of oligonucleotide were introduced to MES suspended microspheres, vortexed and incubated in the presence of 0.5 mg/ml EDAC. Reactions were protected from light in aluminum foil wrapped tubes and incubated at room temperature for 30 min followed by the introduction of additional EDAC to bring the final EDAC concentration to 1 mg/ml. Incubation was continued for an additional 30 min after which beads were washed once with 1 ml 0.02% tween-20 (Sigma) and twice with 0.5 ml 0.1% SDS (Fisher Scientific). Beads were resuspended in 0.5 ml DNAase/RNAase free H2O. Bead suspensions were assessed for aggregation by phase-contrast light microscopy using a Zeiss IM135 inverted microscope.

Detection Protocol: Following completion of sample flow, LFM membranes were allowed to air dry prior to scanning with a standard flatbed PC scanner (CanoScan 9950F, Canon, Inc.). Scans were performed at 2400 dpi resolution using 48 bit color. The resulting image files were converted to grayscale, inverted and saved as 16-bit TIFF files using Photoshop CS2 (Adobe). Image files were then analyzed using GenePix Pro 6.0 (Molecular Devices) to quantify microarray spot intensities for NASBA product detection and for dilution series experiments.

Nucleic Acid Sequence-Based Amplification (NASBA)

NASBA reactions were prepared according to the manufacturer's instructions using the NucliSens Basic kit (Biomerieux) and primer sets at 0.4 µM each. Following a 60 minute incubation at 41° C., NASBA reaction products were detected by using a lateral flow microarray (LFM).

Detection of NASBA reaction products: Detection of NASBA products was accomplished by introducing a 2 µl aliquot of a 20 µl NASBA reaction into 8 µl of LFM running buffer (final buffer composition: 4×SSC, 0.1% SDS, 1.4% Triton X-100, 5% deionized formamide, and 0.5% w/v probe coupled 0.35 µm dyed microspheres). The final volume of solution applied to LFMs was 10 µl. Following completion of sample flow, LFM membranes were allowed to air dry prior to scanning with a standard flatbed PC scanner (CanoScan 9950F, Canon, Inc.). Scans were performed at 2400 dpi resolution using 48 bit color. The resulting image files were converted to grayscale, inverted and saved as 16-bit TIFF files using Photoshop CS2 (Adobe). Image files were then analyzed using GenePix Pro 6.0 (Molecular Devices) to quantify microarray spot intensities for NASBA product detection and for dilution series experiments.

Results:

Oligonucleotides for LFM hybridization sandwich assays were designed to detect NASBA amplified targets corresponding to the *Xylella* XF0324 and *Xanthomonas* XAC1509 signature sequences identified in Example 2. Supported large pore nitrocellulose membranes were patterned with capture oligonucleotides using a NanoPlotter™ 2.0 robotic positioning system (GeSiM, Großerkmannsdorf, Germany) and NanoTip piezoelectronically actuated micropipets (GeSiM). By ejecting droplets from the micropipet at a distance of 500 µm from the nitrocellulose substrate, microarray feature sizes of approximately 200 µm could be generated. In contrast to contact microarray printing methods, this approach preserves the fragile pore structure of the membrane required for microsphere-based detection. Patterned nitrocellulose sheets were cut into 3 mm wide strips and then assembled with conjugate release pads in a custom designed plastic housing. Hybridization-mediated capture of analyte at the cognate capture element of the microarray and non-overlapping hybridization to dyed microsphere conjugated detection oligonucleotide generates a colorimetric signal arising from an increased local concentration of dyed microsphere particles.

Figure 3:
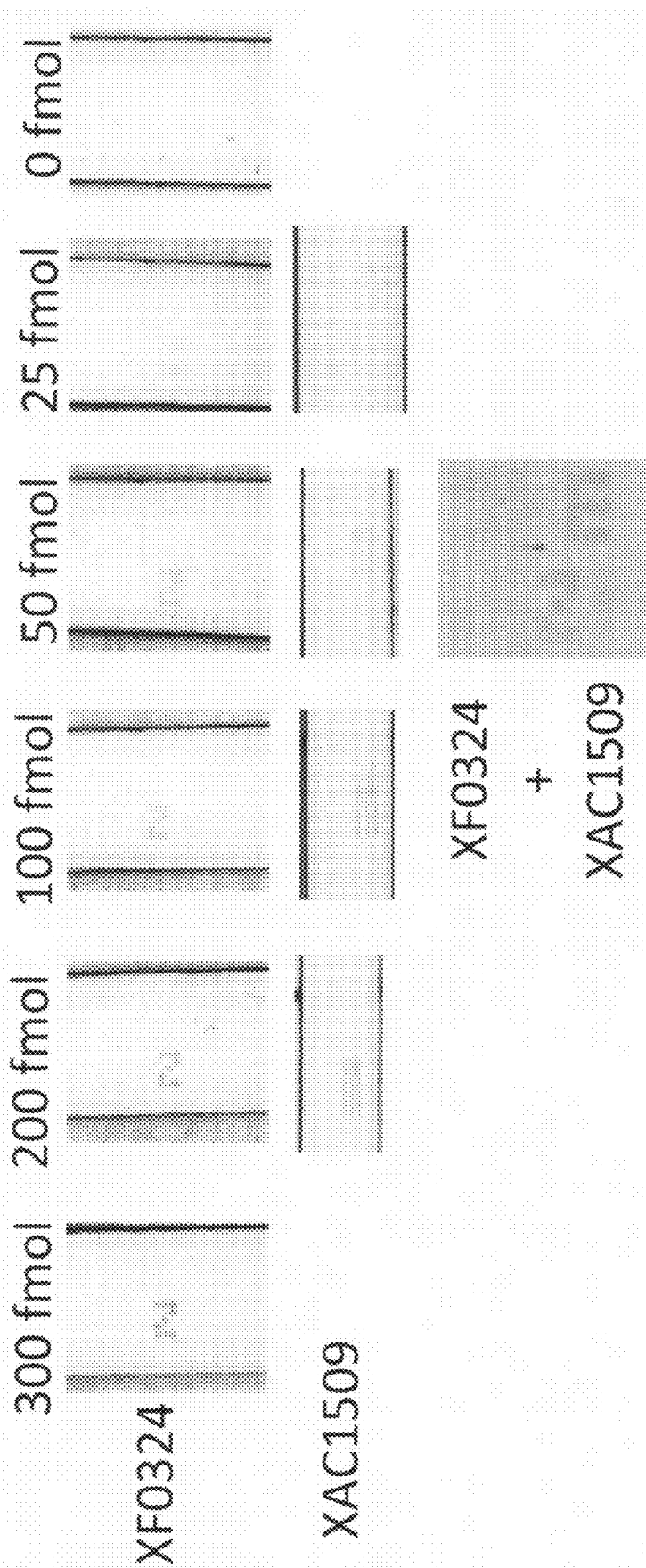
FIG. 3. Characterization of capture and detection oligonucleotide performance using a synthetic DNA analyte. An oligonucleotide incorporating capture and detection probe binding regions of the predicted NASBA amplicons resulting from amplification of Xac or Xf targets were synthesized using standard phosphoramidite synthesis chemistry. The resulting DNA oligonucleotides were quantified and employed as synthetic analyte in LFM assays for the detection of Xac and Xf. These studies consistently revealed detection of 50 fmol or less Xf or Xac analyte when detected alone or together.
Figure 4:
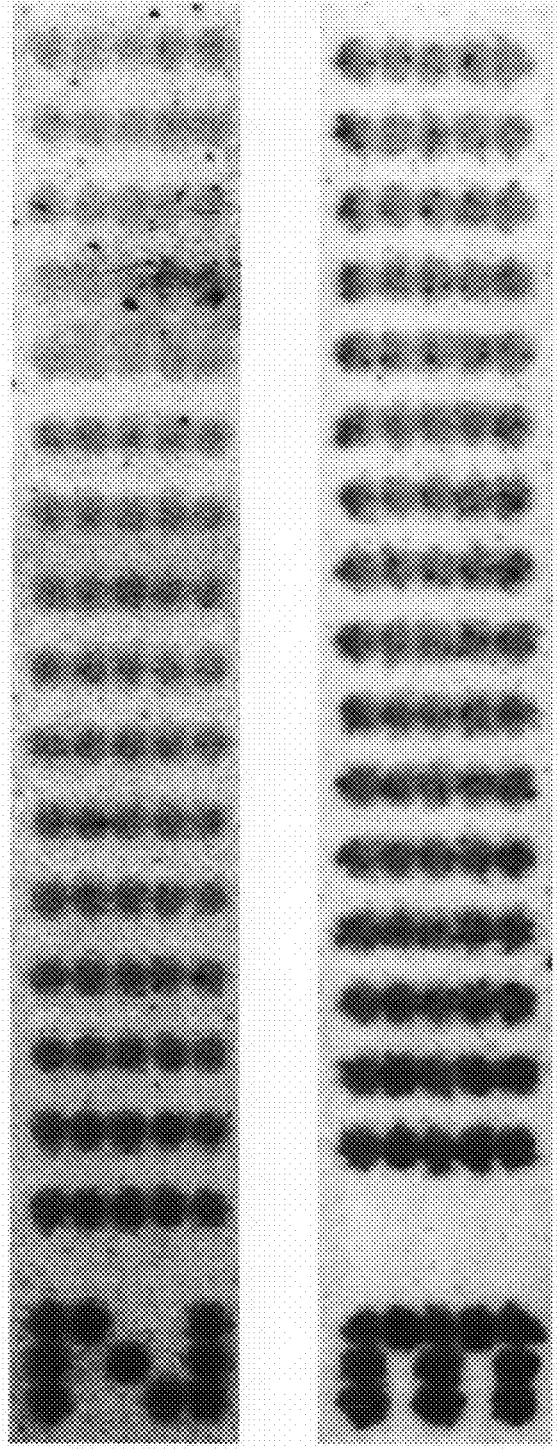
FIG. 4: To test the sensitivity of Xf and Xac NASBA amplicon detection by LFM a synthetic transcript was generated by gene synthesis and cloning of the synthesized fragment in front of a plasmid-borne T7 RNA polymerase promoter. Plasmids were purified from *E. coli*, linearized by restriction with Sca I, and the resulting fragments gel purified and used as template in in vitro transcription reactions. The resulting RNA template was purified, quantified and amplified by NASBA using the corresponding primer sets. Following NASBA amplification, 2 µL of the NASBA reaction was mixed with LFM running buffer and detected by LFM. NASBA reactions programmed with as little as 0.2 attograms of the synthetic template RNA generated positive signals by LFM. The LFMs were air dried and scanned on a flat bed scanner. The images are shown after contract enhancement using the auto levels function of Photoshop® CS3 (Adobe Systems Inc., San Jose, Calif.)

The results presented in FIGS. 3 and 4 show robust detection of both XF0324 and XAC1509 signatures at less than 50 fmol target when challenged with a synthetic DNA oligonucleotide analyte. These results are sufficient to support a sensitive multiplex detection assay for *Xylella fastidiosa* 9a5c and *Xanthomonas axonopodis* pv *citri*. Similarly, NASBA reactions programmed with as little as 0.2 attograms of an in vitro synthesized transcript corresponding the target region of XF0342 and XAC1509 generated robust positive signals (FIG. 4). 0.2 attograms of template corresponds to approximately 1 copy of the XF0342 and XAC1509 sequences.

Figure 5C:
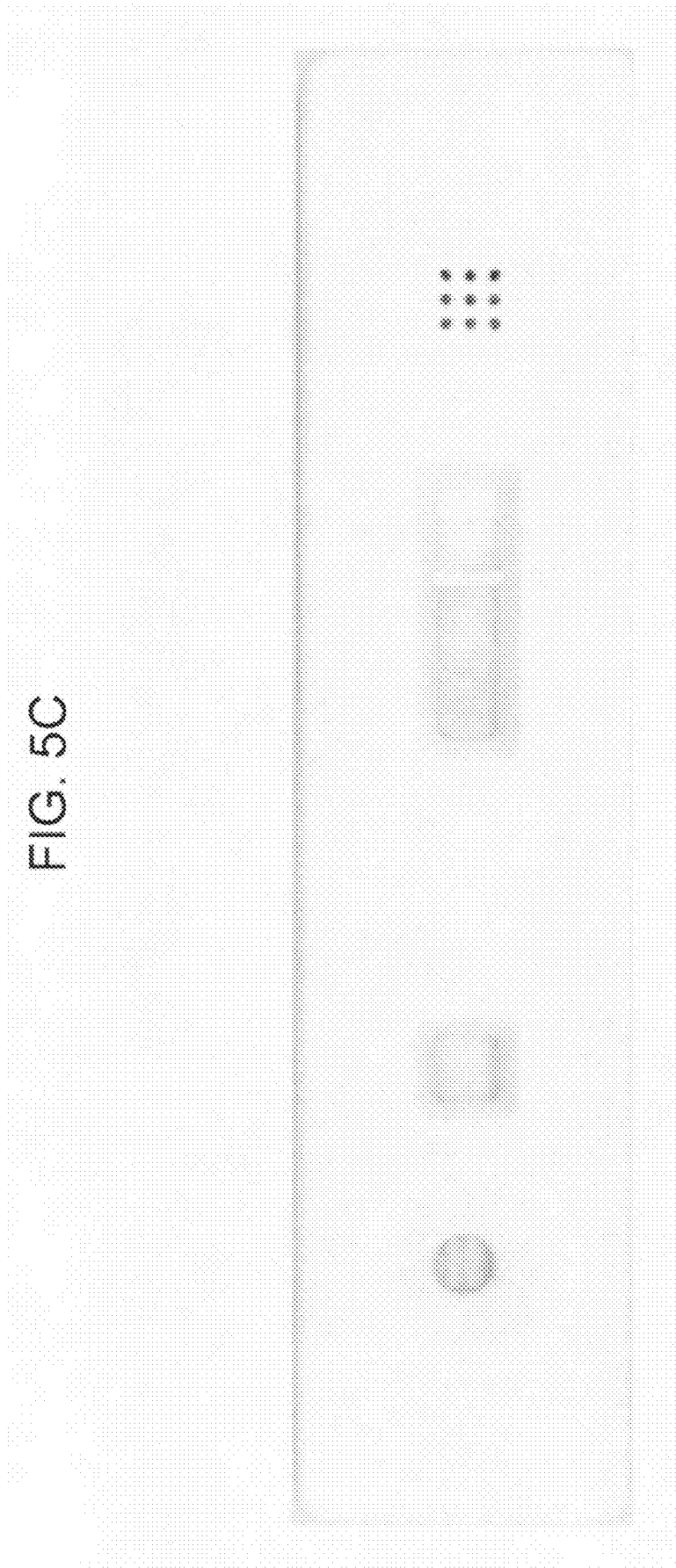
FIG. 5: (A) A schematic representation of Xf and Xac LFM assay design. The 384 element microarray is contained in a 12×32 matrix. In the depicted design, detection oligonucleotides for *X. fastidiosa* strain 9a5c and *X. axonopodis* pv citri are patterned in visually interpretable sets of characters, XF+ and Xac+ respectively. Positive hybridization controls are included to provide visual confirmation of proper assay performance. (B) Lateral flow microarrays patterned as described in part A and challenged with: no template negative control amplification (Neg), *X. fastidiosa* almond strain M12 genomic DNA (M12), *X. fastidiosa* almond strain M23 genomic DNA (M23), *X. fastidiosa* strain 9a5c genomic DNA (Xf 9a5c), *X. axonopodis* pv citri genomic DNA (Xac), and multiplexed detection of *X. axonopodis* pv citri and *X. fastidiosa* strain 9a5c genomic DNA (Xac+Xf 9a5c). Only *X. fastidiosa* strain 9a5c and *X. axonopodis* pv citri genomic DNA generate positive signals on the microarray. (C) Photograph of a prototype assay device for multiplex analysis of *Xylella fastidiosa* and *Xanthomonas axonopodis* pv citri showing assay's visual readout following application of amplicons resulting from multiplexed amplification of *X. fastidiosa* (strain 9a5c) and *X. axonopodis* pv citri sequences as well as positive and negative control indicators.

To test the specificity of signature sequences for the strains of interest, the capacity of amplification primers for XF0324 to fuel amplification from genomic DNA from *X. fastidiosa* strain 9a5c and two *X. fastidiosa* almond strains was examined. Additionally, XAC1509 primers were examined for their ability to amplify their target from Xac genomic DNA preparations. These studies revealed successful amplification and detection of Xf strain 9a5c but not the assayed almond strains (FIG. 5). Similarly, the assays successfully detected Xac genomic DNA (FIG. 5).

Example 4

Lateral Flow Concentration of TMV Particles Contained within Leaf Tissue and Amplification of DNA In this Example, the utility of lateral flow facilitated immuno-capture as a means of concentrating analyte prior to nucleic acid isolation or amplification was investigated with tobacco mosaic virus (TMV).

Materials and Methods:

TMV immuno-assay strips (Agdia, Inc., Elkhart, Ind.) were run using 200 µL of the indicated dilution (FIG. 6) of tobacco extract generated using 100 mg of dried tobacco in 3 ml extract buffer. Reverse-transcriptase PCR (RT-PCR) was used to examine regions below, at and above the TMV capture zone (CZ) (see FIG. 6), using previously reported primer sets for TMV detection (Jacobi, V., G. D. Bachand, et al., 1998, *Development of a multiplex immunocapture RT-PCR assay for detection and differentiation of tomato and tobacco mosaic tobamoviruses*. J Virol Methods 74(2): 167-78). Neat tobacco extract was added directly to RT-PCR reactions. Dilutions of 1:200 and greater were negative by immuno-assay (FIG. 6A).

Results:

The results are shown in FIG. 6, which depicts the results of immuno-affinity capture and concentration of tobacco mosaic virus (TMV) particles during lateral flow of 200 µL of crude macerated tobacco and subsequent amplification (reverse-transcriptase-PCR) reactions programmed with regions of the lateral flow substrate below, at and above the immuno-capture zone. The capture zone is greatly enriched in virus particles while the relative concentration of inhibitory constituents is reduced.

Neat tobacco extract added directly to RT-PCR reactions was negative for TMV without prior immuno-capture to deplete inhibitors. Consistent with this interpretation, 1:50 dilutions of extract were positive by PCR, presumably due to lower inhibitor concentrations. 200 µL of extract dilutions subjected to lateral flow immuno-capture resulted in positive detection at dilutions of up to 1:20,000. The 1000-fold reduction of sample volume from 200 µL to 200 nL exhibited in this study will also facilitate subsequent washing to further reduce inhibitor concentrations.

Significantly, neat extract generated positive PCR reactions only at and above the CZ while the region below the CZ was negative, presumably due to PCR inhibition. These data demonstrate that simple lateral flow immuno-capture without washes or further manipulation can alleviate PCR inhibition both through concentration of target particles and through physical sequestration of inhibitory matrix constituents. Significantly, the region above the CZ in the neat extract generates a positive PCR reaction apparently as a result of viral particle bleed-through and a concomitant depletion of inhibitors. Accordingly, lateral flow can be used to not only concentrate dilute analytes to a spatially defined capture zone but that regions of the device downstream of the capture zone are depleted with respect to the captured species.

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE OF SEQUENCES

SEQ ID NO 1: XF0324-F-P1: NASBA PRIMER 1 for the detection of *Xylella fastidiosa* 9a5c strain:
5'aaTTCTAATACGACTCACTATAGG-GAGAaggCGAAGCACTCACTTCTTCATAGGTCA3'

SEQ ID NO 2: XF0324-F-P2: NASBA PRIMER 2 for the detection of *Xylella fastidiosa* 9a5c strain
5'CCATTTTATGGTGTGGGCGca 3'

SEQ ID NO 3: CAPTURE PROBE for *Xylella* assay:
5'NH2-ttt ttt ttt ttt ttt GGTGATTGCTGATTACCAGCGC 3'

SEQ ID NO 4: DETECTION PROBE for *Xylella* assay:
5'TTGCATCCTGGAACTAAAGT ttt ttt ttt ttt ttt-NH2 3'

SEQ ID NO 5: Predicted amplification product in *Xylella* assay:
CGAAGCACTCACTTCTTCATAGGT-CACTTTAGTTCCAGGATGCAAGCGCTGGTA ATCAGCAATCACCAAAGCAAACATGTC-CAAGTCGTTGGAACCTTGAATGCGCAG TTGC-GAGGTGGCCGCCCTTTGGGTTGAAAAAT-GTCGCACCTCACCAGGATGCG CCCACACCATAAAATGG SEQ ID NO 6: XAC1509-F-P1: NASBA PRIMER 1 for the detection of *Xanthomonas axonopodis* pv *citri* strain:
5'aaT TCT AAT ACG ACT CAC TAT AGG G AGA agg TTTTGAGTGCGCGTTGCTA 3'

SEQ ID NO 7: XAC1509-F-P2: NASBA PRIMER 2 for the detection of *Xanthomonas axonopodis* pv *citri* strain:
5'GGGTCACAACCTGAGAAATCTCTA 3'

SEQ ID NO 8: CAPTURE PROBE for *Xanthamonas* assay:
XAC1509-F-D: 5'NH2-ttt ttt ttt ttt ttt ATGTGGC-CCTATCGCCATCG 3'

SEQ ID NO 9: DETECTION PROBE for *Xanthamonas* assay:
5'GTTGATTCCATCCTCAGAGAC ttt ttt ttt ttt ttt-NH2 3'

What is claimed is:

1. An assay for detecting the presence of *Xylella fastidiosa* strain 9a5c in a citrus plant, an environmental sample or an insect, comprising:
   (a) extracting or releasing nucleic acid from a sample of the citrus plant, environmental sample or insect;
   (b) amplifying a XF0324 gene target nucleic acid using nucleic acid sequence based amplification (NASBA) with the amplification primers of SEQ ID NOS: 1 and 2, to generate a solution containing amplified single-stranded RNA amplification product complementary to the target nucleic acid, if present in the nucleic acid from the sample; and,
   (c) detecting the presence of the RNA amplification product using (i) a detectably-labeled detection oligonucleotide which comprises a sequence complementary to a first sequence of the RNA amplification product, and (ii) a capture oligonucleotide which comprises a sequence complementary to a second sequence of the RNA amplification product.

2. The assay according to claim 1, wherein the capture oligonucleotide comprises the nucleotide sequence of SEQ ID NO: 3 or nucleotides 16-37 thereof.

3. The assay according to claim 1, wherein the detection oligonucleotide comprises the nucleotide sequence of SEQ ID NO: 4 or nucleotides 1-20 thereof.

4. The assay according to claim 1, wherein the capture oligonucleotide comprises the nucleotide sequence of SEQ ID NO: 3 and the detection oligonucleotide comprises the nucleotide sequence of SEQ ID NO: 4.

5. The assay according to claim 1, wherein the sample is selected from the group consisting of a foliar tissue sample, a flower tissue sample, a fruit tissue sample, a xylem tissue sample, a xylem fluid sample, an insect tissue sample and an insect fluid sample.

6. An assay for detecting the presence of *Xanthomonas axonopodis* pv, citri in a citrus plant, an environmental sample or an insect, comprising:
   (a) extracting or releasing nucleic acid from a sample of the citrus plant, environmental sample or insect;
   (b) amplifying a XAC1509 gene target nucleic acid using nucleic acid sequence based amplification (NASBA) with the amplification primers of SEQ ID NOS: 6 and 7, to generate a solution containing amplified single-stranded RNA amplification product complementary to the target nucleic acid, if present in the nucleic acid from the sample; and,
   (c) detecting the presence of the RNA amplification product using (i) a detectably-labeled detection oligonucleotide which comprises a sequence complementary to a first sequence of the RNA amplification product, and (ii) a capture oligonucleotide which comprises a sequence complementary to a second sequence of the RNA amplification product.

7. The assay according to claim 6, wherein the capture oligonucleotide comprises the nucleotide sequence of SEQ ID NO: 8 or nucleotides 16-35 thereof.

8. The assay according to claim 6, wherein the detection oligonucleotide comprises the nucleotide sequence of SEQ ID NO: 9 or nucleotides 1-21 thereof.

9. The assay according to claim 6, wherein the capture oligonucleotide comprises the nucleotide sequence of SEQ ID NO: 8 or nucleotides 16-35 thereof, and the detection oligonucleotide comprises the nucleotide sequence of SEQ ID NO: 9 or nucleotides 1-21 thereof.

10. The assay according to claim 6, wherein the sample is selected from the group consisting of a foliar tissue sample, a flower tissue sample, a fruit tissue sample, a canker sample, a canker-like lesion sample, a xylem tissue sample, a xylem fluid sample, an insect tissue sample and an insect fluid sample.

11. A multiplex assay for detecting the presence of a Citrus Variegated Chlorosis-associated strain of *Xylella fastidiosa* and/or a Citrus Canker-associated strain of *Xanthomonas axonopodis* in a citrus plant, an environmental sample or an insect, comprising:
   (a) extracting or releasing nucleic acid from a sample of the citrus plant, environmental sample or the insect;
   (b) amplifying XF0324 and XAC1509 gene target nucleic acids using nucleic acid sequence based amplification (NASBA) with the amplification primers of SEQ ID NOS: 1 and 2, and SEQ ID NOS: 6 and 7, respectively, to generate a solution containing amplified single-stranded RNA amplification product(s) complementary to the target nucleic acid(s), if present in the nucleic acid from the sample;
   (c) detecting the presence of the RNA amplification product(s) using,
      (i) a detectably-labeled detection oligonucleotide comprising SEQ ID NO: 4 to hybridize to a first sequence in an RNA amplification product corresponding to the XF0324 gene target, and a detectably-labeled detection oligonucleotide comprising SEQ ID NO: 9 to hybridize to a first sequence in an RNA amplification product corresponding to the XAC1509 gene target, and
      (ii) a capture oligonucleotide comprising SEQ ID NO: 3 to hybridize to a second sequence in an RNA amplification product corresponding to the XF0324 gene target, and a capture oligonucleotide comprising SEQ ID NO: 8 to hybridize to a second sequence in an RNA amplification product corresponding to the XAC1509 gene target.

12. The assay according to claim 11, wherein the tissue sample is selected from the group consisting of a foliar tissue sample, a flower tissue sample, a fruit tissue sample, a canker, a canker-like lesion, a xylem tissue sample, a xylem fluid sample, an insect tissue sample and an insect fluid sample.

13. A method of diagnosing citrus variegated chlorosis in a citrus plant, comprising detecting *Xylella fastidiosa* strain 9a5c using the assay according to claim 1, wherein the detection of *Xylella fastidiosa* strain 9a5c provides an indication of the presence of citrus verigated chlorosis in the citrus plant.

14. A method of diagnosing citrus canker in a citrus plant, comprising detecting *Xanthomonas axonopodis* pv citri using the assay according to claim 6, wherein the detection of *Xylella fastidiosa* strain 9a5c provides an indication of the presence of citrus canker in the citrus plant.

* * * * *

SEQUENCE LISTING

<160> NUMBER OF SEQ ID NOS: 31

<210> SEQ ID NO 1
<211> LENGTH: 57
<212> TYPE: DNA
<213> ORGANISM: Artificial
<220> FEATURE:
<223> OTHER INFORMATION: synthetic amplification primer

<400> SEQUENCE: 1
aattctaata cgactcacta tagggagaag gcgaagcact cacttcttca taggtca      57

<210> SEQ ID NO 2
<211> LENGTH: 21
<212> TYPE: DNA
<213> ORGANISM: Artificial
<220> FEATURE:
<223> OTHER INFORMATION: synthetic amplification primer

<400> SEQUENCE: 2
ccattttatg gtgtgggcgc a                                             21

<210> SEQ ID NO 3
<211> LENGTH: 37
<212> TYPE: DNA
<213> ORGANISM: Artificial
<220> FEATURE:
<223> OTHER INFORMATION: synthetic oligonucleotide hybridization
      capture probe

<400> SEQUENCE: 3
tttttttttt tttttggtga ttgctgatta ccagcgc                            37

<210> SEQ ID NO 4
<211> LENGTH: 35
<212> TYPE: DNA
<213> ORGANISM: Artificial
<220> FEATURE:
<223> OTHER INFORMATION: synthetic oligonucleotide hybridization
      detection probe

<400> SEQUENCE: 4
ttgcatcctg gaactaaagt tttttttttt ttttt                              35

<210> SEQ ID NO 5
<211> LENGTH: 178
<212> TYPE: DNA
<213> ORGANISM: Xylella fastidiosa

<400> SEQUENCE: 5
cgaagcactc acttcttcat aggtcacttt agttccagga tgcaagcgct ggtaatcagc   60
aatcaccaaa gcaaacatgt ccaagtcgtt ggaaccttga atgcgcagtt gcgaggtggc  120
cgccctttgg gttgaaaaat gtcgcacctc accaggatgc gcccacacca taaaatgg    178

<210> SEQ ID NO 6
<211> LENGTH: 50
<212> TYPE: DNA
<213> ORGANISM: Artificial
<220> FEATURE:
<223> OTHER INFORMATION: synthetic amplification primer

<400> SEQUENCE: 6
aattctaata cgactcacta tagggagaag gttttgagtg cgcgttgcta              50

```
<210> SEQ ID NO 7
<211> LENGTH: 24
<212> TYPE: DNA
<213> ORGANISM: Artificial
<220> FEATURE:
<223> OTHER INFORMATION: synthetic amplification primer

<400> SEQUENCE: 7
gggtcacaac ctgagaaatc tcta                                          24

<210> SEQ ID NO 8
<211> LENGTH: 35
<212> TYPE: DNA
<213> ORGANISM: Artificial
<220> FEATURE:
<223> OTHER INFORMATION: synthetic oligonucleotide hybridization
      capture probe

<400> SEQUENCE: 8
tttttttttt tttttatgtg gccctatcgc catcg                              35

<210> SEQ ID NO 9
<211> LENGTH: 36
<212> TYPE: DNA
<213> ORGANISM: Artificial
<220> FEATURE:
<223> OTHER INFORMATION: synthetic oligonucleotide hybridization
      detection probe

<400> SEQUENCE: 9
gttgattcca tcctcagaga cttttttttt tttttt                             36

<210> SEQ ID NO 10
<211> LENGTH: 25
<212> TYPE: DNA
<213> ORGANISM: Artificial
<220> FEATURE:
<223> OTHER INFORMATION: Computationally-derived amplification primer

<400> SEQUENCE: 10
cgaagcactc acttcttcat aggtc                                         25

<210> SEQ ID NO 11
<211> LENGTH: 19
<212> TYPE: DNA
<213> ORGANISM: Artificial
<220> FEATURE:
<223> OTHER INFORMATION: Computationally-derived amplificaiton primer

<400> SEQUENCE: 11
ccattttatg gtgtgggcg                                                19

<210> SEQ ID NO 12
<211> LENGTH: 25
<212> TYPE: DNA
<213> ORGANISM: Artificial
<220> FEATURE:
<223> OTHER INFORMATION: Computationally-derived amplification primer

<400> SEQUENCE: 12
tctgtgttcc gtcagtcata agaat                                         25

<210> SEQ ID NO 13
<211> LENGTH: 23
<212> TYPE: DNA
<213> ORGANISM: Artificial
<220> FEATURE:
```

```
<223> OTHER INFORMATION: Computationally-derived amplification primer

<400> SEQUENCE: 13
gcagtctggt tgcgttaact gta                                            23

<210> SEQ ID NO 14
<211> LENGTH: 25
<212> TYPE: DNA
<213> ORGANISM: Artificial
<220> FEATURE:
<223> OTHER INFORMATION: Computationally-derived amplification primer

<400> SEQUENCE: 14
ggtcaatcac tttccctaac tctgt                                          25

<210> SEQ ID NO 15
<211> LENGTH: 24
<212> TYPE: DNA
<213> ORGANISM: Artificial
<220> FEATURE:
<223> OTHER INFORMATION: Computationally-derived amplification primer

<400> SEQUENCE: 15
gatggattta gcctatttaa ccgg                                           24

<210> SEQ ID NO 16
<211> LENGTH: 25
<212> TYPE: DNA
<213> ORGANISM: Artificial
<220> FEATURE:
<223> OTHER INFORMATION: Computationally-derived amplification primer

<400> SEQUENCE: 16
tcaagttgag atccacaaga actgt                                          25

<210> SEQ ID NO 17
<211> LENGTH: 20
<212> TYPE: DNA
<213> ORGANISM: Artificial
<220> FEATURE:
<223> OTHER INFORMATION: Computationally-derived amplification primer

<400> SEQUENCE: 17
ttccatttgc gccaagatag                                                20

<210> SEQ ID NO 18
<211> LENGTH: 25
<212> TYPE: DNA
<213> ORGANISM: Artificial
<220> FEATURE:
<223> OTHER INFORMATION: Computationally-derived amplification primer

<400> SEQUENCE: 18
tgtgtacaac atatcgcata tccag                                          25

<210> SEQ ID NO 19
<211> LENGTH: 23
<212> TYPE: DNA
<213> ORGANISM: Artificial
<220> FEATURE:
<223> OTHER INFORMATION: Computationally-derived amplification primer

<400> SEQUENCE: 19
gtatctgcaa gtgctcaatt cca                                            23

<210> SEQ ID NO 20
```

```
<211> LENGTH: 25
<212> TYPE: DNA
<213> ORGANISM: Artificial
<220> FEATURE:
<223> OTHER INFORMATION: Computationally-derived amplification primer

<400> SEQUENCE: 20
tgataagcat taataggagc gatca                                              25

<210> SEQ ID NO 21
<211> LENGTH: 21
<212> TYPE: DNA
<213> ORGANISM: Artificial
<220> FEATURE:
<223> OTHER INFORMATION: Computationally-derived amplification primer

<400> SEQUENCE: 21
gtggtttgat taatggggca g                                                  21

<210> SEQ ID NO 22
<211> LENGTH: 25
<212> TYPE: DNA
<213> ORGANISM: Artificial
<220> FEATURE:
<223> OTHER INFORMATION: Computationally-derived amplification primer

<400> SEQUENCE: 22
tgctcgtatc ttcaagtaaa ttggc                                              25

<210> SEQ ID NO 23
<211> LENGTH: 23
<212> TYPE: DNA
<213> ORGANISM: Artificial
<220> FEATURE:
<223> OTHER INFORMATION: Computationally-derived amplification primer

<400> SEQUENCE: 23
ggacaccata cttgaagccg tta                                                23

<210> SEQ ID NO 24
<211> LENGTH: 25
<212> TYPE: DNA
<213> ORGANISM: Artificial
<220> FEATURE:
<223> OTHER INFORMATION: Computationally-derived amplification primer

<400> SEQUENCE: 24
tgaatgtgtt caatgtactg aacga                                              25

<210> SEQ ID NO 25
<211> LENGTH: 23
<212> TYPE: DNA
<213> ORGANISM: Artificial
<220> FEATURE:
<223> OTHER INFORMATION: Computationally-derived amplification primer

<400> SEQUENCE: 25
gaaatcgtat gacgcagtta ggc                                                23

<210> SEQ ID NO 26
<211> LENGTH: 25
<212> TYPE: DNA
<213> ORGANISM: Artificial
<220> FEATURE:
<223> OTHER INFORMATION: Computationally-derived amplification primer

<400> SEQUENCE: 26
```

```
ggagtaccat tcctcagtaa gttgc                                           25

<210> SEQ ID NO 27
<211> LENGTH: 20
<212> TYPE: DNA
<213> ORGANISM: Artificial
<220> FEATURE:
<223> OTHER INFORMATION: Computationally-derived amplification primer

<400> SEQUENCE: 27
tcttggcgta ttcatccgtc                                                 20

<210> SEQ ID NO 28
<211> LENGTH: 25
<212> TYPE: DNA
<213> ORGANISM: Artificial
<220> FEATURE:
<223> OTHER INFORMATION: Computationally-derived amplification primer

<400> SEQUENCE: 28
gtggctgaag atattaatga cccac                                           25

<210> SEQ ID NO 29
<211> LENGTH: 21
<212> TYPE: DNA
<213> ORGANISM: Artificial
<220> FEATURE:
<223> OTHER INFORMATION: Computationally-derived amplification primer

<400> SEQUENCE: 29
gatctcagag tccaacggca a                                               21

<210> SEQ ID NO 30
<211> LENGTH: 25
<212> TYPE: DNA
<213> ORGANISM: Artificial
<220> FEATURE:
<223> OTHER INFORMATION: Computationally-derived amplification primer

<400> SEQUENCE: 30
gggtcacaac ctgagaaatc tctat                                           25

<210> SEQ ID NO 31
<211> LENGTH: 18
<212> TYPE: DNA
<213> ORGANISM: Artificial
<220> FEATURE:
<223> OTHER INFORMATION: Computationally-derived amplification primer

<400> SEQUENCE: 31
tttgagtgcg cgttgcta                                                   18
```